US012802819B2

(12) United States Patent
Kosaka et al.

(10) Patent No.: US 12,802,819 B2
(45) Date of Patent: Nov. 17, 2026

(54) MACHINE LEARNING MODEL GENERATION APPARATUS, MACHINE LEARNING MODEL GENERATION METHOD, AND NON-TRANSITORY COMPUTER READABLE MEDIUM

(71) Applicant: NEC Corporation, Tokyo (JP)

(72) Inventors: Yuki Kosaka, Tokyo (JP); Shinto Eguchi, Tokyo (JP)

(73) Assignee: NEC CORPORATION, Tokyo (JP)

(*) Notice: Subject to any disclaimer, the term of this patent is extended or adjusted under 35 U.S.C. 154(b) by 693 days.

(21) Appl. No.: 18/210,428

(22) Filed: Jun. 15, 2023

(65) Prior Publication Data

US 2023/0420129 A1 Dec. 28, 2023

(30) Foreign Application Priority Data

Jun. 22, 2022 (JP) ................................ 2022-099982

(51) Int. Cl.
*G16H 50/20* (2018.01)

(52) U.S. Cl.
CPC .................................. *G16H 50/20* (2018.01)

(58) Field of Classification Search
CPC ........ G16H 10/00–80/00; G06Q 10/00–50/00; G06N 3/00–99/00
USPC ............................ 705/7.11–7.42; 706/1–902
See application file for complete search history.

(56) References Cited

U.S. PATENT DOCUMENTS

| | | | | |
|---|---|---|---|---|
| 9,330,336 | B2 * | 5/2016 | Tajbakhsh | G06N 20/00 |
| 11,269,898 | B1 * | 3/2022 | Salaka | G06N 20/20 |
| 2005/0102246 | A1 * | 5/2005 | Movellan | G06V 40/165 382/118 |

(Continued)

FOREIGN PATENT DOCUMENTS

| | | | | |
|---|---|---|---|---|
| JP | 2002-163374 | A | | 6/2002 |
| JP | 2013-081683 | A | | 5/2013 |
| JP | 2022135733 | A | * | 9/2022 |

OTHER PUBLICATIONS

Htike, Kyaw Kyaw. "Efficient determination of the number of weak learners in AdaBoost." Journal of Experimental & Theoretical Artificial Intelligence 29.5 (2017): 967-982. (Year: 2017).*

(Continued)

*Primary Examiner* — Alan S Miller
(74) *Attorney, Agent, or Firm* — Sughrue Mion, PLLC

(57) ABSTRACT

A machine learning model generation apparatus includes: a movement unit that performs movement processing of moving a sample, having an output error of a (t+1)-th order machine learning model with respect to observation data at time t+1 being larger than a predetermined amount, from the target sample group to a source sample group; and a generation unit that generates a plurality of weak learners by using at least observation data of a sample included in the target sample group after the movement processing and a sample included in the source sample group after the movement processing, and generates a t-th order machine learning model, based on at least each of the plurality of weak learners, and a classification error being evaluated, for each of the plurality of weak learners, by using observation data at time t of the sample included in the target sample group after the movement processing.

14 Claims, 17 Drawing Sheets

(56) References Cited

U.S. PATENT DOCUMENTS

| | | | | |
|---|---|---|---|---|
| 2010/0042561 | A1* | 2/2010 | Abe | G06N 20/20 706/12 |
| 2013/0097107 | A1 | 4/2013 | Kobayashi | |
| 2015/0012472 | A1 | 1/2015 | Liang et al. | |
| 2017/0053211 | A1 | 2/2017 | Heo et al. | |
| 2021/0073036 | A1* | 3/2021 | Kim | G06N 20/20 |
| 2022/0327422 | A1* | 10/2022 | Skogstad | G06N 3/09 |

OTHER PUBLICATIONS

JP Official Communication for JP Application No. 2022-099982, mailed on Mar. 17, 2026 with English Translation.

* cited by examiner

900' 902 100

$$\arg\min \frac{1}{n}\sum_{i=1}^{n} \frac{Y_{t+1i} + \left(\sum_{j=t+2}^{T} Y_{ji}\right) \prod_{j=t+2}^{T} \mathbb{I}\left(A_{ji} = D^{*}{}_{j}\left(X_{ji}\right)\right)}{\prod_{j=t+1}^{T} \pi_{A_{ji}}\left(X_{ji}\right)} \frac{Y_i}{\pi_{A_i}(X_i)} \exp\left(-\frac{1}{K} z_i{}^{T} f(X_i)\right)$$

Fig. 6

Fig. 8 d_TG

| T SAMPLE | OBSERVATION DATA | | | | |
|---|---|---|---|---|---|
| | TIME j=1 | … | TIME j=t | … | TIME j=T |
| i=1 | {X_11, A_11, Y_11} | … | {X_t1, A_t1, Y_t1} | … | {X_T1, A_T1, Y_T1} |
| i=2 | {X_12, A_12, Y_12} | … | {X_t2, A_t2, Y_t2} | … | {X_T2, A_T2, Y_T2} |
| i=4 | {X_14, A_14, Y_14} | … | {X_t4, A_t4, Y_t4} | … | {X_T4, A_T4, Y_T4} |
| … | | | | | |
| i=n | {X_1i, A_1i, Y_1i} | … | {X_ti, A_ti, Y_ti} | … | {X_Ti, A_Ti, Y_Ti} |

d_SG

| S SAMPLE | OBSERVATION DATA | | | | |
|---|---|---|---|---|---|
| | TIME j=1 | … | TIME j=t | … | TIME j=T |
| i=3 | {X_13, A_13, Y_13} | … | {X_t3, A_t3, Y_t3} | … | {X_T3, A_T3, Y_T3} |

d_NG

| N SAMPLE | OBSERVATION DATA | | | | |
|---|---|---|---|---|---|
| | TIME j=1 | … | TIME j=t | … | TIME j=T |
| i=5 | {X_15, A_15, Y_15} | … | {X_t5, A_t5, Y_t5} | … | {X_T5, A_T5, Y_T5} |

Input: Source training data $D_S$, target traninig data $D_T$, the maximum number of iterations $M$, $n_S$ is the number of samples in $D_S$, and $n_T$ is the number of samples in $D_T$

Output: Decision function $D^*$

```
Set α_{S,i} = ½ ln(1 + √(2 ln (n_S / M)))
Initialize the weight vector (w^S, w^T), where w^S = (w_1^S, ··· , w_{n_S}^S), and w^T = (w_1^T, ··· , w_{n_T}^T) to the desired distribution
for t = 1 to M do
    Normalize to 1 the weight vector (w^S, w^T).
    Find the set of candidate weak classifier T that minimizes the classification error over the combined set D_S ∪ D_T, weighted according to (w^S, w^T) using Eq. (8-1)
    Compute the error of T_t on D_T:
        err_t = ε_t = Σ_j^{n_T} ξ_j w_j^T 𝕀[A_j^T ≠ T_t(x_j^T)] / Σ_i^{n_T} ξ_i w_i^T
    α_t = ½ ln ((1 − err_t) / err_t) + log(K − 1)
    Update the weight vector
        w_i^S ← w_i^S e^{−α_{S,i} 𝕀(T_t(x_i^S) ≠ A_i^S)} for D_S
        w_i^T ← w_i^T e^{α_t 𝕀(T_t(x_i^T) ≠ A_i^T)} for D_T
end for
return D*(x) = arg max_k Σ_{m=1}^{M} α_t^{(m)} 𝕀(T^{(m)}(x) = k)
```

where $$\xi_i = \frac{Y_{t+1i} + \left(\sum_{j=t+2}^{T} Y_{ji}\right) \prod_{j=t+2}^{T} \mathbb{I}\left(A_{ji} = D^*{}_j(X_{ji})\right)}{\prod_{j=t+1}^{T} \pi_{A_{ji}}(X_{ji})} \frac{Y_i}{\pi_{A_i}(X_i)}$$

Fig. 11

Algorithm 3 Cooporative Outcome Weighted Learning (COWL)

Input: Source training data $D_S$, target traninig data $D_T$, the maximum number of iterations $M$, $n_S$ is the number of samples in $D_S$, and $n_T$ is the number of samples in $D_T$

Output: Decision function $D^*$

Set $\alpha_{S,i} = \frac{1}{2}\ln(1 + \sqrt{2\ln\frac{n_S}{M}})\tau_i$, where $\tau_i = |D^*_{t+1}(x_{t+1,i}) - A_{t+1,i}|$ Initialize the weight vector $(\mathbf{w}^S, \mathbf{w}^T)$, where $\mathbf{w}^S = (w_1^S, \cdots, w_{n_S}^S)$, and $\mathbf{w^T} = (w_1^T, \cdots, w_{n_T}^T)$ to the desired distribution for $t = 1$ to $M$ do

Normalize to 1 the weight vector $(\mathbf{w}^S, \mathbf{w}^T)$.

Find the set of candidate weak classifier $T$ that minimizes the classification error over the combined set $D_S \cup D_T$, weighted according to $(\mathbf{w}^S, \mathbf{w}^T)$ using Eq. (12)

Compute the error of $T_t$ on $D_T$:

$\text{err}_t = \epsilon_t = \sum_j^{n_T} \xi_j w_j^T \mathbb{I}[A_j^T \neq T_t(x_j^T)] / \sum_i^{n_T} \xi_i w_i^T$ $\alpha_t = \frac{1}{2}\ln\frac{1-\text{err}_t}{\text{err}_t} + \log(K-1)$ Update the weight vector $w_i^S \leftarrow w_i^S e^{-\alpha_{S,i}\mathbb{I}(T_t(x_i^S) \neq A_i^S)}$ for $D_S$ $w_i^T \leftarrow w_i^T e^{\alpha_t \mathbb{I}(T_t(x_i^T) \neq A_i^T)}$ for $D_T$ end for return $D^*(x) = \arg\max_k \sum_{m=1}^{M} \alpha_t^{(m)} \mathbb{I}(T^{(m)}(x) = k)$ where $\xi_i = \frac{S_{t+1,i} + \left(\sum_{j=t+2}^{T} Y_{ji}\right) \prod_{j=t+2}^{T} \mathbb{I}\left(A_{ji} = D^*{}_j(X_{ji})\right)}{\prod_{j=t+1}^{T} \pi_{A_{ji}}(X_{ji})} \frac{Y_i}{\pi_{A_i}(X_i)}$

Fig. 12

900'' 902 100

$$\arg\min \frac{1}{n}\sum_{i=1}^{n} \frac{S_{t+1,i} + \left(\sum_{j=t+2}^{T} Y_{ji}\right) \prod_{j=t+2}^{T} \mathbb{I}\left(A_{ji} = D^{*}{}_{j}(X_{ji})\right)}{\prod_{j=t+1}^{T} \pi_{A_{ji}}(X_{ji})} \frac{Y_i}{\pi_{A_i}(X_i)} \exp\left(-\frac{1}{K} z_i{}^{T} f(X_i)\right)$$

$$S_{t+1,i} = \begin{cases} Y_{(t+1),i} & if\ \mathbb{I}\left(A_{(t+1)i} = D^{*}{}_{t+1}(X_{t+1,i})\right) \quad i \in Target, \\ \lambda Y_{(t+1),i} & if\ \mathbb{I}\left(A_{(t+1)i} \neq D^{*}{}_{t+1}(X_{t+1,i})\right) \quad i \in Source, \\ 0 & otherwise \end{cases}$$

120

Fig. 13

130

$$\arg\min \frac{1}{n}\sum_{i=1}^{n} \left( \frac{Y_{t+1i} + \left(\sum_{j=t+2}^{T} Y_{ji}\right) \prod_{j=t+2}^{T} \mathbb{I}\left(A_{ji} = D^{*}{}_{j}(X_{ji})\right)}{\prod_{j=t+1}^{T} \pi_{A_{ji}}(X_{ji})} \frac{Y_i}{\pi_{A_i}(X_i)} C^{*}\left(A_i, D^{*}(X_i)\right) \right. \\ \left. \exp\left(-\frac{1}{K} z_i{}^{T} f(X_i)\right) \right)$$

Fig. 14

Algorithm 5 Cost-sensitive Cooperative Outcome Weighted Learning(CCOWL)

Input: Source training data $D_S$, target traninig data $D_T$, the maximum number of iterations $M$, $n_S$ is the number of samples in $D_S$, and $n_T$ is the number of samples in $D_T$

Output: Decision function $D^*$

Set $\alpha_S = \frac{1}{2}\ln(1 + \sqrt{2\ln\frac{n_S}{M}})$, $\tau_i = |D^*_{t+1}(x_{t+1,i}) - A_{t+1,i}|$ Initialize the weight vector $(\mathbf{w}^S, \mathbf{w}^T)$, where $\mathbf{w}^S = (w_1^S, \cdots, w_{n_S}^S)$, and $\mathbf{w}^T = (w_1^T, \cdots, w_{n_T}^T)$ to the desired distribution for $t = 1$ to $M$ do

Normalize to 1 the weight vector $(\mathbf{w}^S, \mathbf{w}^T)$.

Find the set of candidate weak classifier $T$ that minimizes the classification error over the combined set $D_S \cup D_T$, weighted according to $(\mathbf{w}^S, \mathbf{w}^T$ $C^*(A_i, T^{(m)}(x_i)), \xi_i)$ Compute the error of $T_t$ on $D_T$:

$\mathrm{err}_t = \sum_j^{n_T} \left\{C^*(A_j, T^{(m)}(x_j))\xi_j\right\} w_j^T \mathbb{I}[A_j^T \neq T_t(x_j^T)] / \sum_i^{n_T} \left\{C^*(A_i, T^{(m)}(x_i))\xi_i\right\} w_i^T$ $\alpha_t = \frac{1}{2}\ln\frac{1-\mathrm{err}_t}{\mathrm{err}_t} + \log(K-1)$ Update the weight vector $w_i^S \leftarrow w_i^S e^{-\alpha_S \tau_i \mathbb{I}(T_t(x_i^S) \neq A_i^S)}$ for $D_S$ $w_i^T \leftarrow w_i^T e^{\alpha_t \mathbb{I}(T_t(x_i^T) \neq A_i^T)}$ for $D_T$ end for return $D^*(x) = \arg\max_k \sum_{m=1}^{M} \alpha_t^{(m)} \mathbb{I}(T^{(m)}(x) = k)$ $$\text{where } \xi_i = \frac{Y_{t+1i} + \left(\sum_{j=t+2}^{T} Y_{ji}\right) \prod_{j=t+2}^{T} \mathbb{I}\left(A_{ji} = D^*{}_j(X_{ji})\right)}{\prod_{j=t+1}^{T} \pi_{A_{ji}}(X_{ji})} \frac{Y_i}{\pi_{A_i}(X_i)}$$

Fig. 15

900 901 904 902 903

$$\arg\min \frac{1}{n}\sum_{i=1}^{n} \frac{\left(\sum_{j=t+1}^{T} Y_{ji}\right)\prod_{j=t+1}^{T} \mathbb{I}\left(A_{ji} = D^{*}{}_{j}\left(X_{ji}\right)\right)}{\prod_{j=t+1}^{T} \pi_{A_{ji}}\left(X_{ji}\right)} \frac{Y_i}{\pi_{A_i}\left(X_i\right)} L\left(A_i, f\left(X_i\right)\right)$$

Fig. 18

MACHINE LEARNING MODEL GENERATION APPARATUS, MACHINE LEARNING MODEL GENERATION METHOD, AND NON-TRANSITORY COMPUTER READABLE MEDIUM

INCORPORATION BY REFERENCE

This application is based upon and claims the benefit of priority from Japanese patent application No. 2022-099982, filed on Jun. 22, 2022, the disclosure of which is incorporated herein in its entirety by reference.

TECHNICAL FIELD

The present disclosure relates to a learning model generation apparatus, a learning model generation method, and a program, and particularly, relates to a learning model generation apparatus, a learning model generation method, and a program that generate a learning model for dynamically estimating an action plan.

BACKGROUND ART

In a medical field, a doctor records a treatment plan for treating a disease of a patient and manages an implementation situation of the treatment plan. For example, Patent Literature 1 (Japanese Unexamined Patent Application Publication No. 2002-163374) discloses a disease management system that generates a treatment plan by an operation of a doctor.

SUMMARY

However, in Patent Literature 1 described above, a doctor analyzes a present state from various pieces of information about a patient, and then creates a treatment plan tailored to the patient according to a treatment guideline, and thus a preparation burden is large. In addition, quality of the treatment plan is influenced by an experience value of a doctor. Therefore, it is desired to support creation of a treatment plan in a medical field by automatically generating a treatment plan tailored to a patient by using a learning model. The above-described problems are not limited to the medical field, but are also applicable to an education field, sports training, or the like.

In view of the problems described above, an example object of the present disclosure is to provide a learning model generation apparatus, a learning model generation method, and a program that suitably generate a learning model for creating an action plan tailored to a subject.

In a first example aspect of the present disclosure, a learning model generation apparatus includes:

at least one memory; and at least one processor configured to be constituted in such a way as to execute an instruction stored in the at least one memory, wherein the at least one processor executes movement processing of moving a sample, among a plurality of samples included in a target sample group, having an output error of a (t+1)-th order learning model with respect to observation data at time t+1 (t is a natural number) being larger than a predetermined amount, from the target sample group to a source sample group, processing of generating a plurality of weak learners by using at least observation data from time t to time T of at least one sample included in the target sample group after the movement processing and at least one sample included in the source sample group after the movement processing, and processing of generating a t-th order learning model, based on at least each of the plurality of generated weak learners, and a classification error being evaluated, for each of the plurality of generated weak learners, by using observation data at time t of the at least one sample included in the target sample group after the movement processing, the observation data include at least a state and an action of a sample at a specific time until time T, and the t-th order learning model outputs an action at time t by using at least a state at time t as an input.

In a second example aspect of the present disclosure, a learning model generation method includes:

executing movement processing of moving a sample, among a plurality of samples included in a target sample group, having an output error of a (t+1)-th order learning model with respect to observation data at time t+1 (t is a natural number) being larger than a predetermined amount, from the target sample group to a source sample group;

generating a plurality of weak learners by using at least observation data from time t to time T of at least one sample included in the target sample group after the movement processing and at least one sample included in the source sample group after the movement processing; and generating a t-th order learning model, based on at least each of the plurality of generated weak learners, and a classification error being evaluated, for each of the plurality of generated weak learners, by using observation data at time t of the at least one sample included in the target sample group after the movement processing.

The observation data include at least a state and an action of a sample at a specific time until time T, and the t-th order learning model outputs an action at time t by using at least a state at time t as an input.

In a third example aspect of the present disclosure, a program causes a computer to execute:

movement processing of moving a sample, among a plurality of samples included in a target sample group, having an output error of a (t+1)-th order learning model with respect to observation data at time t+1 (t is a natural number) being larger than a predetermined amount, from the target sample group to a source sample group;

processing of generating a plurality of weak learners by using at least observation data from time t to time T of at least one sample included in the target sample group after the movement processing and at least one sample included in the source sample group after the movement processing; and processing of generating a t-th order learning model, based on at least each of the plurality of generated weak learners, and a classification error being evaluated, for each of the plurality of generated weak learners, by using observation data at time t of the at least one sample included in the target sample group after the movement processing.

The observation data include at least a state and an action of a sample at a specific time until time T, and the t-th order learning model outputs an action at time t by using at least a state at time t as an input.

BRIEF DESCRIPTION OF DRAWINGS

The above and other aspects, features and advantages of the present disclosure will become more apparent from the following description of certain example embodiments when taken in conjunction with the accompanying drawings, in which:

FIG. 6 is a diagram for describing a deriving method of a weak learner included in a t-th order learning model according to the second example embodiment;

FIG. 8 is a diagram illustrating one example of data structure of a storage unit according to the second example embodiment;

FIG. 11 is a diagram illustrating one example of an algorithm for generating a t-th order learning model according to the second embodiment;

FIG. 12 is a diagram illustrating one example of an algorithm for generating a t-th order learning model according to a third example embodiment;

FIG. 13 is a diagram for describing a deriving method of a weak learner included in a t-th order learning model according to a fourth example embodiment;

FIG. 14 is a diagram for describing a deriving method of a weak learner included in a t-th order learning model according to a fifth example embodiment;

FIG. 15 is a diagram illustrating one example of an algorithm for generating a t-th order learning model according to the fifth example embodiment;

FIG. 18 is a diagram for describing a deriving method of an associated t-th order learning model.

EXAMPLE EMBODIMENT

Hereinafter, example embodiments of the present disclosure will be described in detail with reference to the drawings. In each drawing, the same or corresponding elements are denoted by the same reference signs, and redundant descriptions are omitted as necessary for clarity of description.

Problem of Example Embodiment

First, a problem of at least one example embodiment of the present disclosure will be described in detail.

In order to support creation of a treatment plan of a patient in a medical field, automatically creating a treatment plan by a computer has been performed. For example, it has been considered to find a previous treatment plan of a patient suffering from the same disease as a target patient, and to create a similar treatment plan as a treatment plan for the target patient.

However, even in a patient having the same disease, there is a difference in information such as a characteristic and a gene related to the disease. Therefore, it is required to create a treatment plan suitable for each individual, based on patient-specific information. Thus, it is expected to enhance a treatment effect of the patient.

Further, it has been studied to sequentially select a treatment tailored to individual characteristic after start of the treatment, while considering a personal history of a patient. Thus, it is expected that a treatment effect can be further enhanced, and that the treatment with a less burden and cost of a patient can be proposed.

In such a background, a system using a learning model that sequentially and automatically selects a treatment that maximizes a treatment effect of a patient according to a response of the patient has been developed. Note that, the above-described system is not limited to a medical field, but may also be used in an education field, sports training, or the like. Therefore, hereinafter, a term "action" being a superordinate concept is used instead of a term "treatment".

Figure 17:
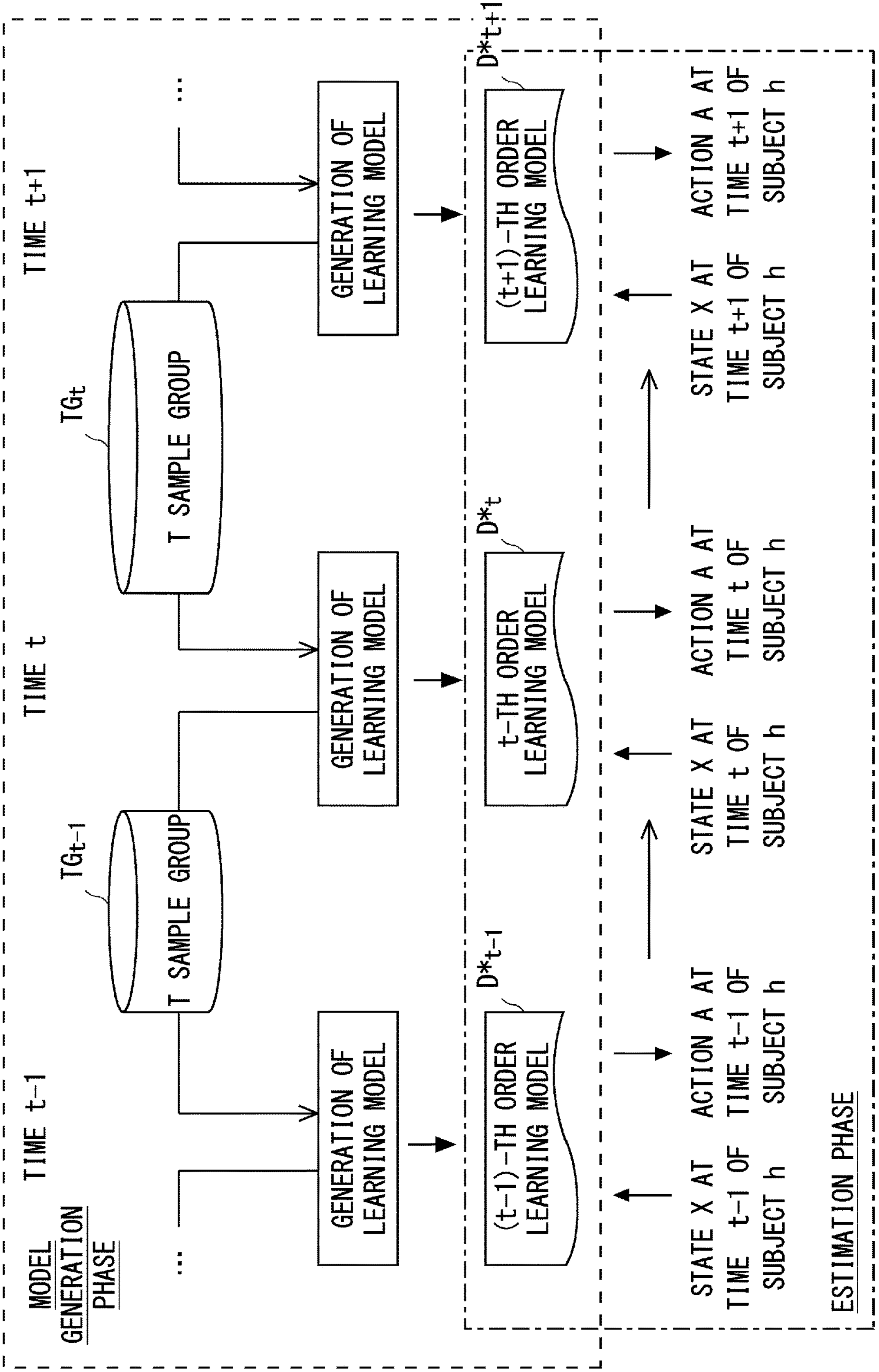
FIG. 17 is a diagram schematically illustrating a flow of processing of an associated system.

FIG. 17 is a diagram schematically illustrating a flow of processing of an associated system.

The system proposes an action to be performed at time j, which maximizes a treatment effect of a patient, by using a learning model that differs for each time j. The time may be absolute time, or may be relative time. When it is the relative time, the time may be referred to as a stage. In addition, the time may refer to a point on a time axis, or may refer to a predetermined period on the time axis. Hereinafter, j is assumed to be a natural number. For example, time j=1 indicates a first day of a treatment, time j=2 indicates a second day of the treatment, time j=t indicates a t-th day of the treatment, and time j=T (where T is a natural number larger than t) may indicate final time, i.e., a final day of the treatment.

For example, a j-th order learning model $D^*_j$ regards a state $X_{jh}$ of a subject h observed at time j as an input. Then, the j-th order learning model $D^*_j$ estimates an action $A_{jh}$ of the subject h at the time j. The estimated action $A_{jh}$ is an action in which a sum of effects acquired by the subject h from the time j to the final time T is maximized. For example, in FIG. 17, a (t−1)-th order learning model $D^*_{t-1}$, a t-th order learning model $D^*_t$, and a (t+1)-th order learning model $D^*_{t+1}$ are illustrated as j-th order learning models associated to times j=t−1, t, and t+1, respectively.

Processing of the system is divided into a model generation phase in which the j-th order learning models at times j=1 to T are generated, and an estimation phase in which an action of the subject h is planned by using the j-th order learning models at times j=1 to T.

(Model Generation Phase)

The j-th order learning model $D^*_j$ is generated by using observation data of a target sample group (hereinafter, referred to as a T sample group) $TG_j$ at time j. The T sample group TG is a set of patients (that is, samples) whose observation data are used as training data at a time of learning. Note that, observation data at the time j of a sample i are represented by a vector $\{X_{ji}, A_{ji}, Y_{ji}\}$ in which a state $X_{ji}$, an action $A_{ji}$, and an effect $Y_{ji}$ are combined with one another. The effect $Y_{ji}$ indicates an amount of an effect acquired by an action of the sample i having a state at a specific time in the time j=1 to T. First, observation data at times j=1 to T for samples of i=1, 2, . . . , n (n is a natural number) are prepared.

For example, observation data of the T sample group $TG_t$ at time t, which is used for generating a t-th order learning model $D^*_t$ when j=t, are training data for learning the t-th order learning model $D^*_t$. The training data for learning the t-th order learning model $D^*_t$ are observation data of a sample included in the T sample group among the samples of i=1, 2, . . . , n (n is a natural number).

Generation of each learning model is performed backward in such a way as to go back in the time j. In other words, the t-th order learning model $D^*_t$ in a case of j=t is generated after the (t+1)-th order learning model $D^*_{t+1}$ in a case of j=(t+1) is generated. In learning of the (t+1)-th order learning model $D^*_{t+1}$, the observation data of a sample included in the T sample group $TG_{t+1}$ associated to the time t+1 are used. Herein, all the observation data of the sample that is not optimal in the (t+1)-th order learning model $D^*_{t+1}$ are discarded without being used in the t-th order learning model $D^*_t$. Therefore, the observation data of the sample included in the T sample group $TG_t$ associated to the time t is a sample acquired by excluding the sample that is not optimal in the (t+1)-th order learning model $D^*_{t+1}$ among the samples included in the T sample group $TG_{t+1}$ associated to the time t+1. In other words, it is a sample being optimal in the (t+1)-th order learning-model $D^*_{t+1}$.

Therefore, generally, the number of samples of the T sample group $TG_t$ associated to the time t is smaller than the number of samples of the T sample group $TG_{t+1}$ associated to the time (t+1). When the number of samples decreases, the number of pieces of observation data used as training data decreases, and therefore it becomes difficult to generate a learning model with high estimation accuracy.

Note that, a "sample that is not optimal in the j-th order learning model $D^*_j$" indicates a sample in which an error between the action $A_{ji}$ included in the observation data and an output of the j-th order learning model $D^*_j$ is larger than a predetermined amount when the state $X_{ji}$ of the sample i included in the observation data is input to the j-th order learning model $D^*_j$. Hereinafter, the error is referred to as an "output error of j-th order learning model $D^*_j$". Hereinafter, as one example, a "sample that is not optimal in the j-th order learning model $D^*_j$" indicates that the output error of the j-th order learning model $D^*_j$ is larger than 0, that is, the j-th order learning model $D^*_j$ has misclassified. In contrast, a "sample being optimal in the j-th order learning model $D^*_j$" indicates a sample in which the output error of the j-th order learning model $D^*_j$ is equal to or less than a predetermined amount. Hereinafter, as one example, a "sample being optimal in the j-th order learning model $D^*_j$" indicates that the $A_{ji}$ included in the observation data matches the output of the j-th order learning model $D^*_j$, that is, the output error is 0.

(Estimation Phase)

On the other hand, estimation of an action is performed forward with a lapse of time j. For example, assuming that current time j is t, an action $A_{th}$ of the subject h at the current time t is acquired by inputting, to the t-th order learning model $D^*_t$, a status $X_{th}$ of the subject h observed at the current time t. Then, when the time has elapsed and the time t+1 is reached, an action $A_{(t+1)h}$ of the subject h at the time t+1 is acquired by inputting a status $X_{(t+1)h}$ of the subject h observed at the time t+1. As described above, an action to be taken is sequentially estimated with a lapse of time. Therefore, an action plan is dynamically created. In a medical field, an action plan of a healthcare worker to be taken for a patient, who is the subject, is dynamically created.

The above-described problem can also be grasped from a mathematical expression.

FIG. 18 is a diagram for describing a deriving method of an associated t-th order learning-model $D^*_t$. The t-th order learning model $D^*_t$ can be derived by the following expression (1).

[Mathematical 1]

$$\arg\min \frac{1}{n} \sum_{i=1}^{n} \frac{\left(\sum_{j=t+1}^{T} Y_{ji}\right) \prod_{j=t+1}^{T} \mathbb{1}(A_{ji} = D_j^*(X_{ji}))}{\prod_{j=t+1}^{T} \pi_{A_{ji}}(X_{ji})} \frac{Y_i}{\pi_{A_i}(X_i)} L(A_i, f(X_i)) \tag{1}$$

Herein, $\pi_{A_{ji}}(X_{ji})$ represents a propensity score. The propensity score represents a probability that the $A_{ji}$ is allocated to the $X_{ji}$.

A function f included in the expression (1) is a function associated to the t-th order learning model $D^*_t$. Therefore, deriving the function f is equivalent to deriving the t-th order learning model $D^*_t$.

A block 900 illustrated in FIG. 18 indicates a sum of effects (rewards) acquired from the time (t+1) to the final time T. In addition, a block 902 indicates an effect (reward) at the time t. In addition, L is a classification loss function, and a block 903 indicates a loss at the time t.

Herein, a block 904 included in a block 901 indicates an output error. The block 901 indicates becoming 1 in a case where the output error is 0 at all times from the time (t+1) to the time T, but becoming 0 in other case. Becoming 0 in the block 901 means that the observation data of the sample are discarded. In other words, when there is a time at which the output error is not 0 even once between the time (t+1) and the time T, the observation data of the sample are discarded at that time. Therefore, it can be understood that the number of samples decreases as the time proceeds backward.

At least one of the following example embodiments solves such a problem.

First Example Embodiment

Figure 1:
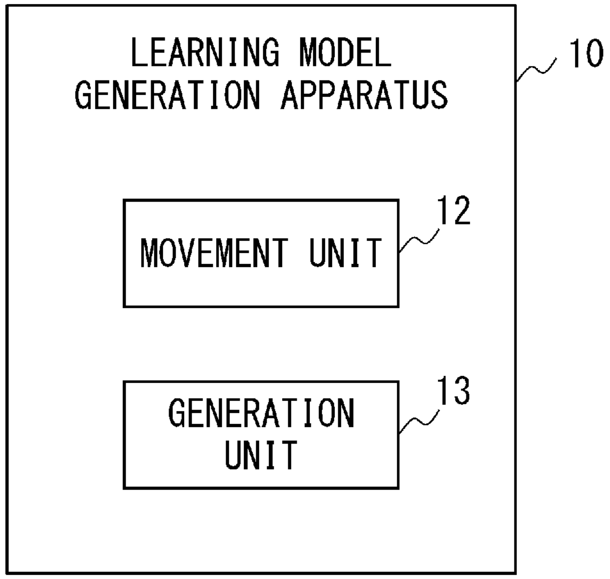
FIG. 1 is a block diagram illustrating a configuration of a learning model generation apparatus according to a first example embodiment.

Next, a first example embodiment of the present disclosure will be described. The first example embodiment may be described as an overview of example embodiments described below. FIG. 1 is a block diagram illustrating a configuration of a learning model generation apparatus 10 according to the first example embodiment. The learning model generation apparatus 10 is a computer apparatus that sequentially generates a learning model associated to each time in order to dynamically create an action plan. Specifically, the learning model generation apparatus 10 generates T j-th order learning models $D^*_j$ by using observation data at times j=1 to T for samples of i=1, 2, . . . , n while going back in time associated to the model ($D^*_T \rightarrow D_{T-1} \rightarrow \ldots \rightarrow D^*_{t+1} \rightarrow D^*_t \rightarrow \ldots \rightarrow D^*_j$). The learning model generation apparatus 10 may be a computer system including one or a plurality of computer apparatuses.

Herein, observation data at any time j of a sample i include at least a status $X_{ji}$ and an action $A_{ji}$ of the sample i at that time j.

In addition, the j-th order learning model $D^*_j$ is a learned model for outputting an action $A_{jh}$ at the time j by inputting at least a state $X_{jh}$ at the time j of a subject h. For example, the j-th order learning model $D^*_j$ is a model obtained by ensembling weak learners. An example of an ensembled model is boosting. Hereinafter, it is assumed that the j-th order learning model $D^*_j$ adopts an AdaBoost algorithm being one example of boosting. In addition, the j-th order learning model $D^*_j$ is described as being represented by a weighted sum of a weak learner.

As illustrated in FIG. 1, the learning model generation apparatus 10 includes a movement unit 12 and a generation unit 13.

The movement unit 12 executes movement processing. The movement processing is processing of moving a sample, among a plurality of samples included in a T sample group, having an output error of a (t+1)-th order learning model $D^*_{t+1}$ with respect to observation data at time t+1 larger than a predetermined amount, from the T sample group to a source sample group. Hereinafter, the source sample group is referred to as an S sample group. In addition, a sample included in the T sample group associated to a predetermined time may be referred to as a T sample, and a sample included in the S sample group associated to a predetermined time may be referred to as an S sample.

In addition, "movement" may be physically to be moved or logically to be moved. Physically to be moved may include changing a storage destination. As logically to be moved, it may be included that an attribute (a belonging destination or a type) of the sample is changed.

In addition, "larger than a predetermined amount" may be, but is not limited to, larger than 0. In other words, the movement unit 12 moves a sample that is not optimal at time t+1 from the T sample group to the S sample group at time t. The T sample group at the time t does not include a sample that is not optimal.

The generation unit 13 generates a t-th order learning model $D^*_t$ by using observation data from the time t to the time T of a sample included in the T sample group and observation data from the time t to the time T of a sample included in the S sample group.

Specifically, the generation unit 13 generates a plurality of weak learners, and generates the t-th order learning model $D^*_t$ by combining the plurality of generated weak learners. The weak learner included in the t-th order learning model $D^*_t$ is regard at least a state $X_{ti}$ at the time t of a subject i as an input, and outputs an action $A_{ti}$ at the time t.

More specifically, first, the generation unit 13 generates a plurality of weak learners by using, as training data, observation data $\{X_{ji}, A_{ji}, Y_{ji}\}$ (j=t, t+1, . . . , T, i=1, 2, . . . , n), from the time t to the time T, of a sample included in the T sample group after the movement processing and a sample included in the S sample group after the movement processing. At this time, the generation unit 13 may use, as the training data, observation data, from the time t to the time T, of all the samples included in the T sample group, or observation data, from the time t to the time T, of some samples. It is similar for the sample included in the S sample group.

Next, for each of the plurality of weak learners, the generation unit 13 evaluates a classification error by using the observation data at the time t of the sample included in the T sample group after the movement processing. In other words, the generation unit 13 calculates a classification error with respect to the T sample.

Finally, the generation unit 13 generates the t-th order learning model $D^*_t$, based on at least each of the plurality of weak learners and an associated classification error. For example, the generation unit 13 generates the t-th order learning model $D^*_t$ by combining the weak learners weighted by a weight associated to the above-described classification error.

Figure 2:
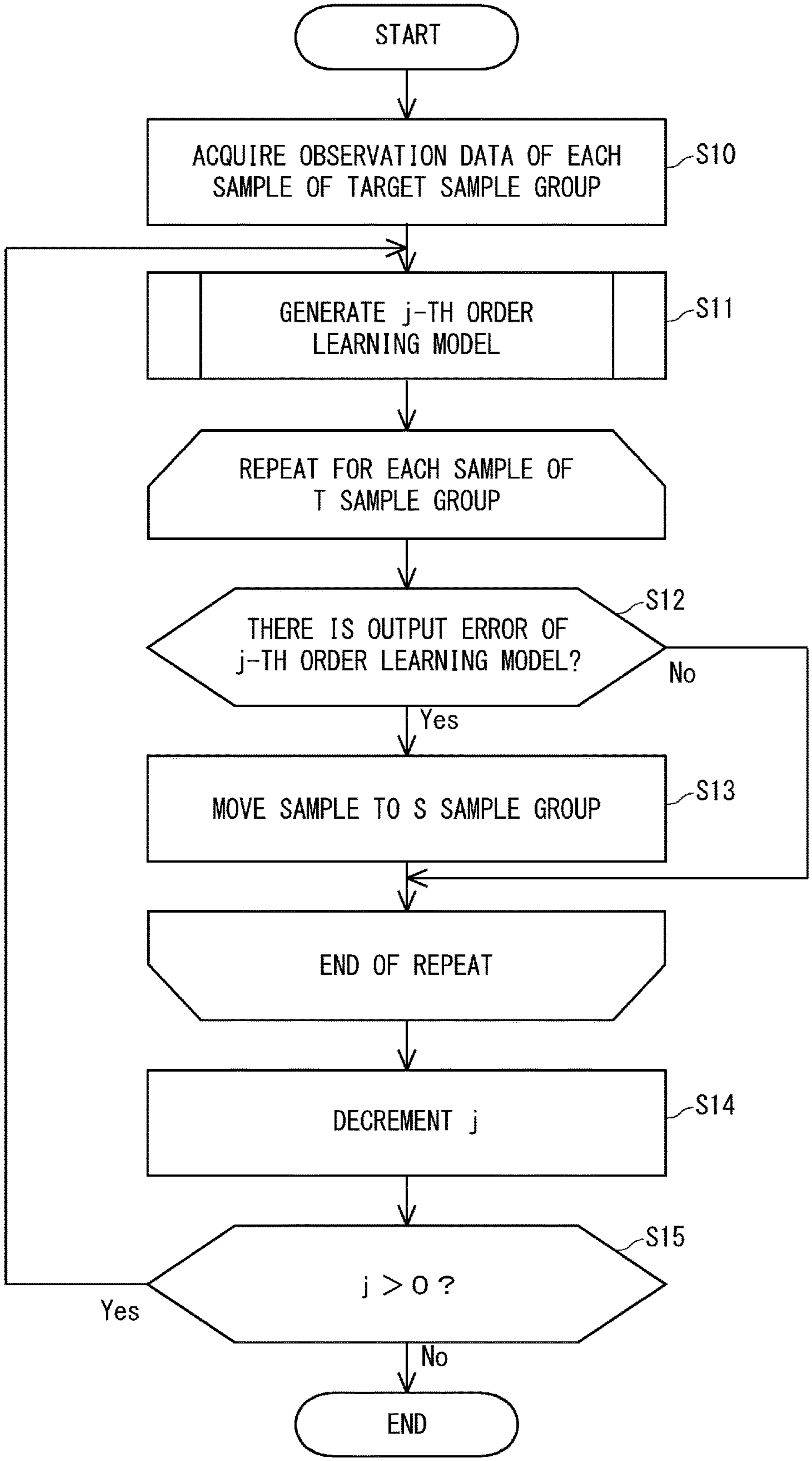
FIG. 2 is a flowchart illustrating a flow of a generation method of a learning model according to the first example embodiment.

FIG. 2 is a flowchart illustrating a flow of a generation method of a learning model according to the first example embodiment. First, the learning model generation apparatus 10 acquires observation data of each sample of the T sample group (S10). Next, the generation unit 13 of the learning model generation apparatus 10 generates the j-th order learning model $D^*_j$ (S11).

Next, the movement unit 12 of the learning model generation apparatus 10 repeats processing illustrated in S12 to S13 for each sample of the T sample group at time j. In S12, the movement unit 12 decides whether there is an output error of the j-th order learning model $D^*_j$ with respect to the observation data at the time j of the sample. Presence of an output error indicates erroneous decision. At this time, the movement unit 12 inputs, to the j-th order learning model $D^*_j$, a state $X_{ji}$ included in the observation data at the time j of a sample i, and calculates, as the output error, a difference between the acquired output value and an action $A_{ji}$ included in the observation data. When there is the output error (Yes in S12), the movement unit 12 moves the sample from the T sample group to the S sample group without discarding the sample (S13). On the other hand, when there is no output error (No in S12), the movement unit 12 does not move the sample from the T sample group to the S sample group, and leaves the sample as it is in the T sample group.

After performing the above processing on all the samples included in the T sample group, the learning model generation apparatus 10 decrements the time j (S14). Then, when the time j is larger than 0 (Yes in S15), the learning model generation apparatus 10 returns the processing to S11, and when the time j becomes 0 (No in S15), the processing ends.

Figure 3:
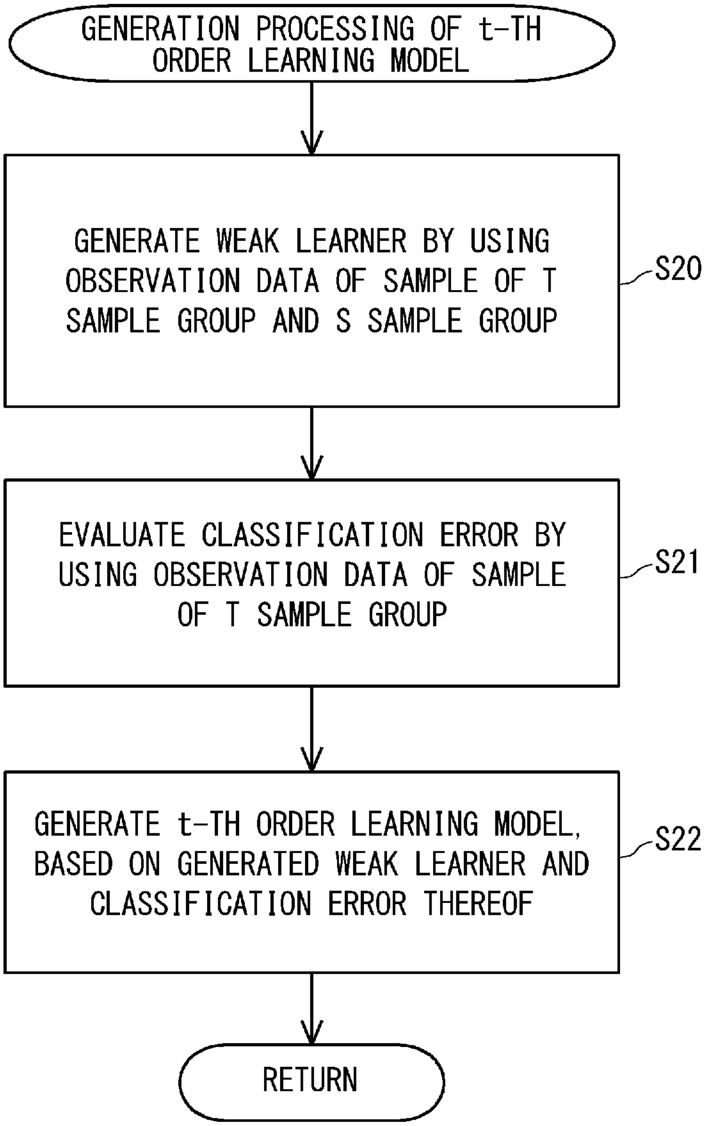
FIG. 3 is a flowchart illustrating a flow of a generation method of a t-th order learning model according to the first example embodiment.

FIG. 3 is a flowchart illustrating a flow of a generation method of a t-th order learning model according to the first example embodiment when j=t. First, the generation unit 13 generates a weak learner by using observation data, from time j=t to time T, of a sample included in the T sample group and the S sample group (S20). Next, the generation unit 13 evaluates, for the weak learner, a classification error by using the observation data at the time t of the plurality of samples included in the T sample group (S21). By S20 to S21, the generation unit 13 generates a plurality of weak learners and a classification error associated to each weak learner. Next, the generation unit 13 generates the t-th order learning model, based on at least the generated weak learner and the associated classification error (S22).

Note that, the generation unit 13 may repeat S20 to S21 by the number of generated weak learners, and then execute S22.

As described above, according to the first example embodiment, in generation of a weak learner included in a learning model associated to target time t, in addition to the T sample, the S sample being determined to be not optimal in the learning model associated to the later time t+1 is used. Note that, the learning model associated to the later time t+1 is generated before the learning model associated to the target time t. Therefore, training data used for learning can be increased. As a result, it is possible to generate a learning model that estimates in highly accuracy an action at each time according to each individual subject.

Second Example Embodiment

Figure 4:
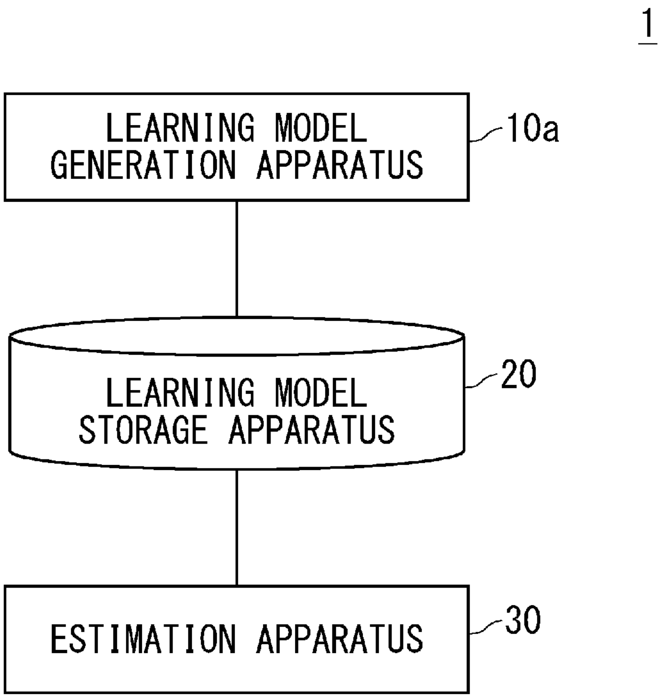
FIG. 4 is a block diagram illustrating an overall configuration of a system according to a second example embodiment.

Next, a second example embodiment of the present disclosure will be described. FIG. 4 is a block diagram illustrating an overall configuration of a system 1 according to the second example embodiment. The system 1 is a computer system for dynamically creating an action plan tailored to each subject. The system 1 includes a learning model generation apparatus 10*a*, a learning model storage apparatus 20, and an estimation apparatus 30. The learning model generation apparatus 10*a*, the learning model storage apparatus 20, and the estimation apparatus 30 are communicably connected to one another.

The learning model generation apparatus 10*a* is one example of the above-described learning model generation apparatus 10. For each time, the learning model generation apparatus 10*a* generates a learning model for estimating an action A to be taken at that time. The action A to be taken is an action that maximizes an effect acquired after the time.

The learning model storage apparatus 20 is a storage apparatus that stores a learning model at each time generated by the learning model generation apparatus 10*a*.

The estimation apparatus 30 dynamically creates an action plan of a subject h. Specifically, the estimation apparatus 30 reads a learning model stored in the learning model storage apparatus 20, and sequentially estimates the action A to be taken by the subject h at a target time by using the read learning model.

Figure 5:
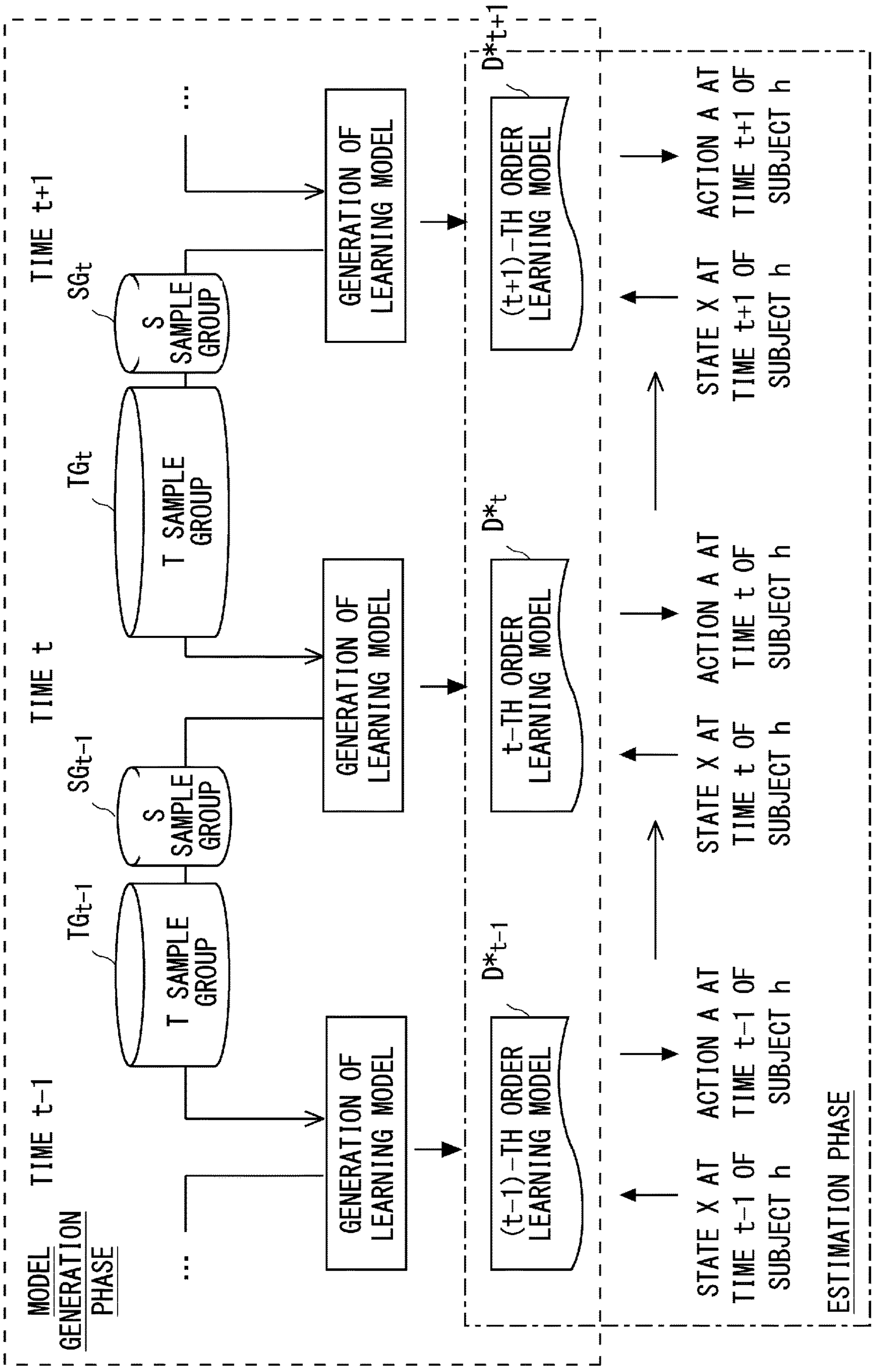
FIG. 5 is a diagram schematically illustrating a flow of processing of the system according to the second example embodiment.

FIG. 5 is a diagram schematically illustrating a flow of processing of the system 1 according to the second example embodiment. The flow of processing of the system 1 according to the second example embodiment is basically similar to the flow of processing illustrated in FIG. 17. The learning model generation apparatus 10*a* executes processing of a model generation phase illustrated by a dotted line in FIG. 5, and the estimation apparatus 30 executes processing of an estimation phase illustrated by a dashed-dotted line in FIG. 5.

In FIG. 5, similarly to FIG. 17, it is illustrated that, from a T sample group $TG_t$, among samples included in a T sample group $TG_{t+1}$ at time t+1, a sample that is not optimal in a (t+1)-th order learning model $D^*_{t+1}$ is excluded. However, in FIG. 5, it is different from FIG. 17 in that, among the samples included in the T sample group $TG_{t+1}$ at the time t+1, the sample that is not optimal in the (t+1)-th order learning model $D^*_{t+1}$ is included in a S sample group $SG_t$ at time t. In the second example embodiment, the S sample group $SG_t$ includes only a sample that is not optimal in the (t+1)-th order learning model $D^*_{t+1}$. In addition to these, however, the S sample group $SG_t$ may include at least some of samples that are not optimal in a learning model associated to later time (e.g., j=t+2).

Then, when generating a t-th order learning model $D^*_t$, the learning model generation apparatus 10*a* uses observation data of the sample included in the S sample group $SG_t$, in addition to observation data of the sample included in the T sample group $TG_t$.

In the second example embodiment, a j-th order learning model $D^*_j$ is expressed by a weighted sum of M weak learners (a first weak learner $T^{(1)}$, a second weak learner $T^{(2)}$, . . . , a M-th weak learner $T^{(M)}$) (M is a natural number). Specifically, the j-th order learning model $D^*_j$ is given by the following equation (2).

[Mathematical 2]

$$D^*_j(X) = \arg\max_k \sum_{m=1}^{M} \alpha_j^{(m)} \mathbb{I}\left(T^{(m)}(X) = k\right) \tag{2}$$

$\alpha_j^{(m)}$ is reliability of a m-th weak learner $T^{(m)}$ constituting the j-th order learning model.

For example, the reliability $\alpha_j^{(m)}$ is given by the following equation (3).

[Mathematical 3]

$$\alpha_j^{(m)} = \frac{1}{2}\ln\frac{1 - err_2^{(m)}}{err_2^{(m)}} + \log(K - 1) \tag{3}$$

K is a total number of classifications, that is, the number of types of an action $A_{ji}$. As indicated in the equation (3), the reliability $\alpha_j^{(m)}$ is calculated based on at least a second classification error $err_2^{(m)}$ of the weak learner $T^{(m)}$. The second classification error $err_2^{(m)}$ is one example of a classification error of the first example embodiment, and is a classification error evaluated for the weak learner $T^{(m)}$ by using observation data at time j of a sample included in the T sample group TG.

For example, the second classification error $err_2^{(m)}$ is given by the following equation (4).

[Mathematical 4]

$$err_2^{(m)} = \epsilon_m = \sum_i^{n_T} \xi_i \omega_i^T \mathbb{I}\left[A_i^T \neq T^{(m)}\left(X_i^T\right)\right] / \sum_i^{n_T} \xi_i \omega_i^T \tag{4}$$

$X_i^T$ and $A_i^T$ each is a condition and an action when a sample i is a sample (T sample) included in the T sample group TG.

Note that, a coefficient $\xi_i$ included in the second classification error $err_2^{(m)}$ is given by the following equation (5).

[Matnematical 5]

$$\xi_i = \frac{Y_{t+1} + \left(\sum_{j=t+2}^{T} Y_{ji}\right)\prod_{j=t+2}^{T} \mathbb{I}\left(A_{ji} = D^*_j(X_{ji})\right)}{\prod_{j=t+1}^{T} \pi_{A_{ji}}(X_{ji})} \frac{Y_i}{\pi_{A_i}(X_i)} \tag{5}$$

FIG. 6 is a diagram for describing a deriving method of the weak learner $T^{(m)}$ included in the t-th order learning model $D^*_t$ according to the second example embodiment.

First, the weak learner $T^{(m)}$ is related with f included in the expression (1). The f included in the expression (1) is given by the following equation (6).

[Mathematical 6]

$$f(X_i) = \sum_{m=1}^{M} \beta^m g^m(X_i) \tag{6}$$

$g^{(m)}(X)$ is a function associated to the weak learner $T^{(m)}$ one-to-one. In other words, learning the weak learner $T^{(m)}$ corresponds to deriving the optimized $g^{(m)}(X)$.

g(X) represents a K-dimensional vector. A relationship between g(X) and T(X) is given by the following equation (7).

[Mathematical 7]

$$T(x)=k,\ \text{if}\ g_k(x)=1,\ g_k(x)=\begin{cases}1, & T(x)=k,\\ -\dfrac{1}{K-1}, & T(x)\neq k.\end{cases} \tag{7}$$

g(X) is a vector in which a k element takes 1 when T(X)=k and the other elements take −1/(K−1).

A deriving expression of the optimized g(X) is given by the following expression (8-1).

[Mathematical 8]

Herein, an example using a multi−class exponential loss $L(z, f)=\exp\left(-\frac{1}{K}z^T f\right)$ to a classification loss function $L$ of the expression (1) is indicated.

$$\arg\min \frac{1}{n}\sum_{i=1}^{n}\frac{Y_{t+1i}+\left(\sum_{j=t+2}^{T}Y_{ji}\right)\prod_{j=t+2}^{T}\mathbb{I}\left(A_{ji}=D_j^*(X_{ji})\right)}{\prod_{j=t+2}^{T}\pi_{A_{ji}}(X_{ji})}\frac{Y_i}{\pi_{A_i}(X_i)}\exp\left(-\frac{1}{K}z_i^T f(X_i)\right) \tag{8-1}$$

$$\arg\min \frac{1}{n}\sum_{i=1}^{n}\frac{Y_{t+1i}+\left(\sum_{j=t+2}^{T}Y_{ji}\right)\prod_{j=t+2}^{T}\mathbb{I}\left(A_{ji}=D_j^*(X_{ji})\right)}{\prod_{j=t+2}^{T}\pi_{A_{ji}}(X_{ji})}\frac{Y_i}{\pi_{A_i}(X_i)}\omega_i^{m-1}\exp\left(-\frac{1}{K}\beta^m z_i^T g^m(X_i)\right) \tag{8-2}$$

Then, the expression (8-1) can be expressed, by using m weak learners, as following.

$\beta^m$ is a parameter for the m-th weak learner. $z_i$ represents $A_{ti}$ of a sample i. Herein, z represents a K-dimensional vector, and is given by the following equation (9).

[Mathematical 9]

$$\mathcal{Z}=\left\{\begin{array}{c}\left(1,-\frac{1}{K-1},\ldots\right)^T,\\ \left(-\frac{1}{K-1},1,-\frac{1}{K-1},\ldots\right)^T,\\ \left(-\frac{1}{K-1},-\frac{1}{K-1},\ldots,1\right)^T\end{array}\right\} \tag{9}$$

When $A_{ti}$=k, the z vector is a vector in which a k element takes 1 and the other elements take −1/(K−1).

An objective function indicated after arg min may be referred to as a first classification error $err_1$. The first classification error $err_1$ corresponds to a classification error evaluated for the weak learner $T^{(m)}$ by using observation data at time t of the T sample and observation data at time t of the S sample.

Deriving the optimized g(X) corresponds to deriving g(X) that minimizes the first classification error $err_1$.

A block 900', included in FIG. 6, corresponding to the expression (8) corresponds to the blocks 900 and 901, included in FIG. 18, corresponding to the expression (1). In addition, a block 902, included in FIG. 6, corresponding to the expression (8) is similar to the block 902, included in FIG. 18, corresponding to the expression (1). However, FIG. 6 is different from FIG. 18 in that a block 100 is included instead of the block 903. The block 100 indicates a loss at time t for the sample i.

$\omega_i$ included in the block 100 is a weight to be added to the loss for the sample i. $\omega_i^{m-1}$ is given by an equation (10).

[Mathematical 10]

$$\omega_i^{m-1}=\exp\left(-\frac{1}{K}Z_i^T f^{(m-1)}(X_i)\right) \tag{10}$$

Note that, f is a weighted sum of m−1, and is given by the following equation (11).

[Mathematical 11]

$$f^{(m-1)}(X_i)=\beta^1 g^1(X_i)+\beta^2 g^2(X_i)+\ldots+\beta^{m-1}g^{m-1}(X_i) \tag{11}$$

The weight $\omega_i$ indicates a degree of influence of observation data of the sample i on optimization of g(X) (that is, learning of a weak learner T(X)). In the second example embodiment, the weight $\omega_i$ may be updated every time when one learned weak learner is generated. A manner of updating is different depending on whether the sample i is classified as a T sample or an S sample at associated time. A weight is set as $\omega_i^T$ when the sample i is the T sample, and a weight is set as $\omega_i^S$ when the sample i is the S sample.

Figure 7:
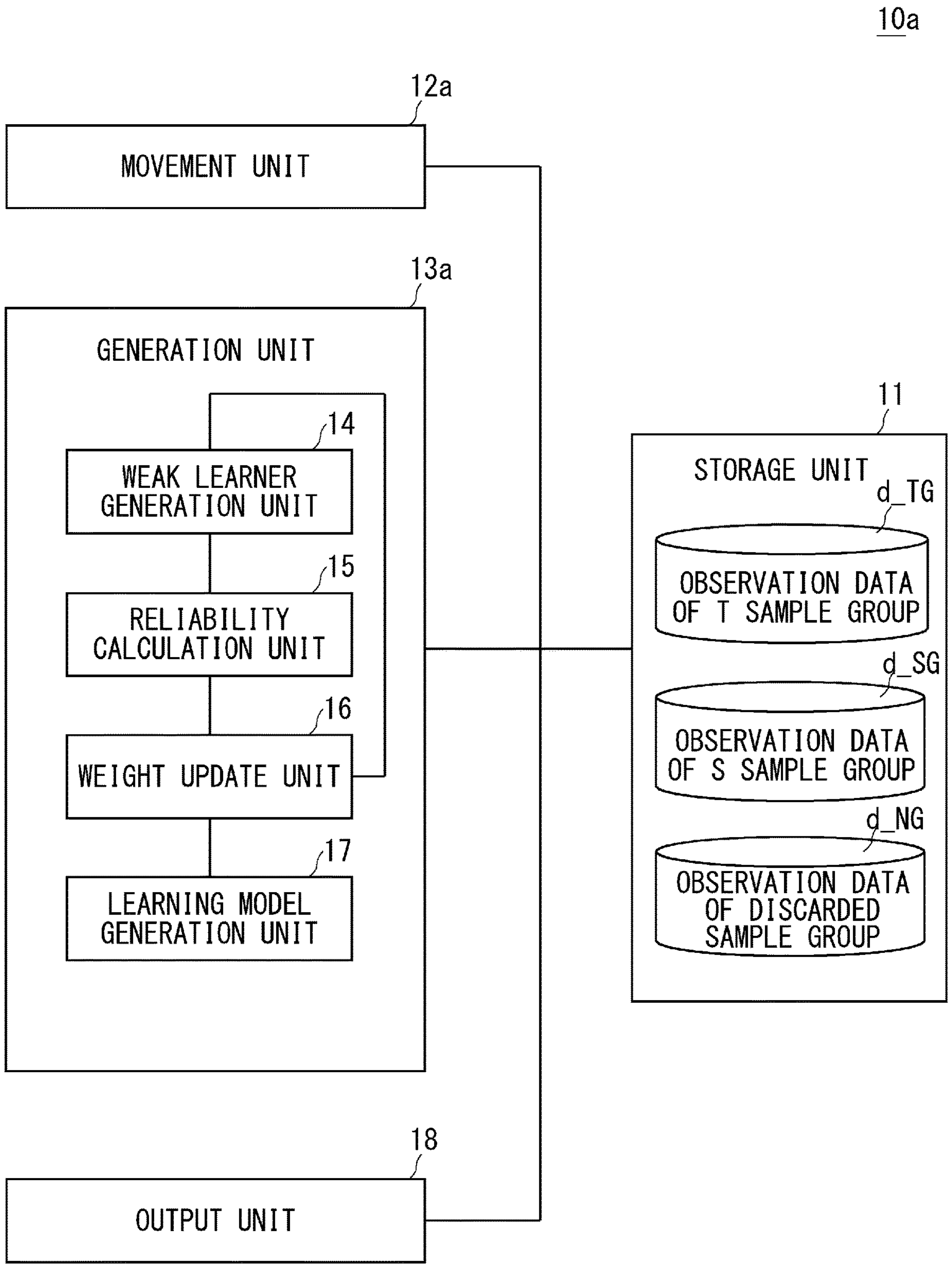
FIG. 7 is a block diagram illustrating a configuration of a learning model generation apparatus according to the second example embodiment.

FIG. 7 is a block diagram illustrating a configuration of the learning model generation apparatus 10_a_ according to the second example embodiment. The learning model generation apparatus 10_a_ includes a storage unit 11, a movement unit 12_a_, a generation unit 13_a_, and an output unit 18.

The storage unit 11 is a storage apparatus that stores observation data of samples i=1 to n at time j=1 to T.

The movement unit 12_a_ is one example of the movement unit 12 described above. The generation unit 13_a_ is one example of the generation unit 13 described above. The generation unit 13_a_ includes a weak learner generation unit 14, a reliability calculation unit 15, a weight update unit 16, and a learning model generation unit 17. The movement unit 12_a_ and the generation unit 13_a_ sequentially generate a j-th order learning model $D^*_j$ backward from j=T, and output the generated j-th order learning model $D^*_j$ to the output unit 18.

The output unit 18 outputs the generated j-th order learning model $D^*_j$. In addition, the output unit 18 stores the generated j-th order learning model $D^*_j$ in a learning model storage apparatus 20.

FIG. 8 is a diagram illustrating one example of data structure of the storage unit 11 according to the second example embodiment. Observation data stored in the storage unit 11 are {state $X_{ji}$, action $A_{ji}$, effect $Y_{ji}$} of samples i=1 to n at time j=1 to T. The observation data are divided into observation data d_TG of a sample (T sample) of the T sample group TG, observation data d_SG of a sample (S sample) of the S sample group SG, and observation data d_NG of a sample (N sample) of a discarded sample group (N sample group) NG.

At a time point of generating a T-th order learning model $D^*_T$ associated to final time j=T, all the samples are included in the T sample group TG. Then, all the observation data stored in the storage unit 11 are classified into the observation data d_TG. Then, at this time, the number of samples included in the S sample group SG is 0, and the observation data d_SG do not exist. In addition, at this time, the number of samples included in the N sample group NG is 0, and the observation data d_NG do not exist.

Then, as j associated to the generated learning model decreases, the number of samples included in the T sample group TG decreases, and the number of samples included in any of the S sample group SG and the N sample group NG increases. Therefore, as j decreases, the number of pieces of observation data classified into the observation data d_TG decreases, and the number of pieces of observation data classified into any of the observation data d_SG and the observation data d_NG increases.

Note that, the sample included in the S sample group SG is a sample that is not optimal by a learning model associated to a time (for example, time t+1) immediately after a time (for example, time t) associated to the learning model to be generated.

Next, specific processing of each element will be described with reference to FIGS. 9 to 11.

Figure 9:
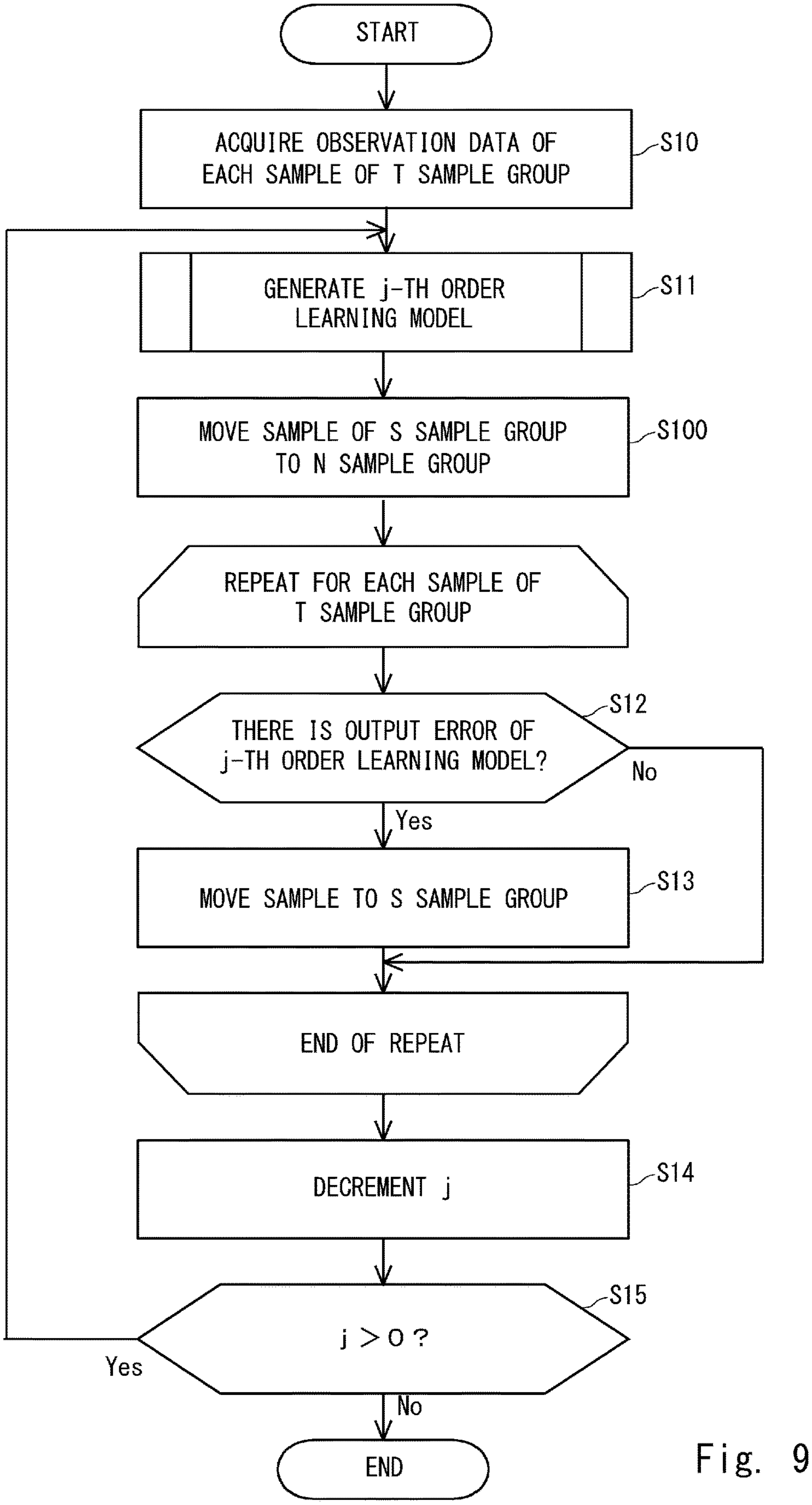
FIG. 9 is a flowchart illustrating a flow of a generation method of a learning model according to the second example embodiment.

First, FIG. 9 is a flowchart illustrating a flow of a generation method of a learning model according to the second example embodiment. Steps illustrated in FIG. 9 includes S100, in addition to the steps illustrated in FIG. 2.

In S100, the movement unit 12*a* moves a sample of the S sample group SG to the N sample group NG, and discards a sample included in the S sample group SG. Specifically, the movement unit 12*a* re-classifies observation data classified as the observation data d_SG into the observation data d_NG. Initialization of the S sample group SG makes it possible to consider only a sample that is optimal until the latest but is not optimal only the latest, in generation of the learning model. As a result, it is possible to suppress an influence on decrease in estimation accuracy of a learning model due to use of observation data of a non-optimal sample as training data, and to suitably increase the training data.

Note that, in S12 to S13, the movement unit 12*a* moves a sample of the T sample group TG in which an output error of the (t+1)-th order learning model $D^*_{t+1}$ occurs with respect to the observation data at the time t+1, from the T sample group TG to the S sample group SG. Specifically, the movement unit 12*a* re-classifies, into the observation data d_SG, the observation data being classified as the observation data d_TG in which the output error of the (t+1)-th order learning model $D^*_{t+1}$ occurs.

Figure 10:
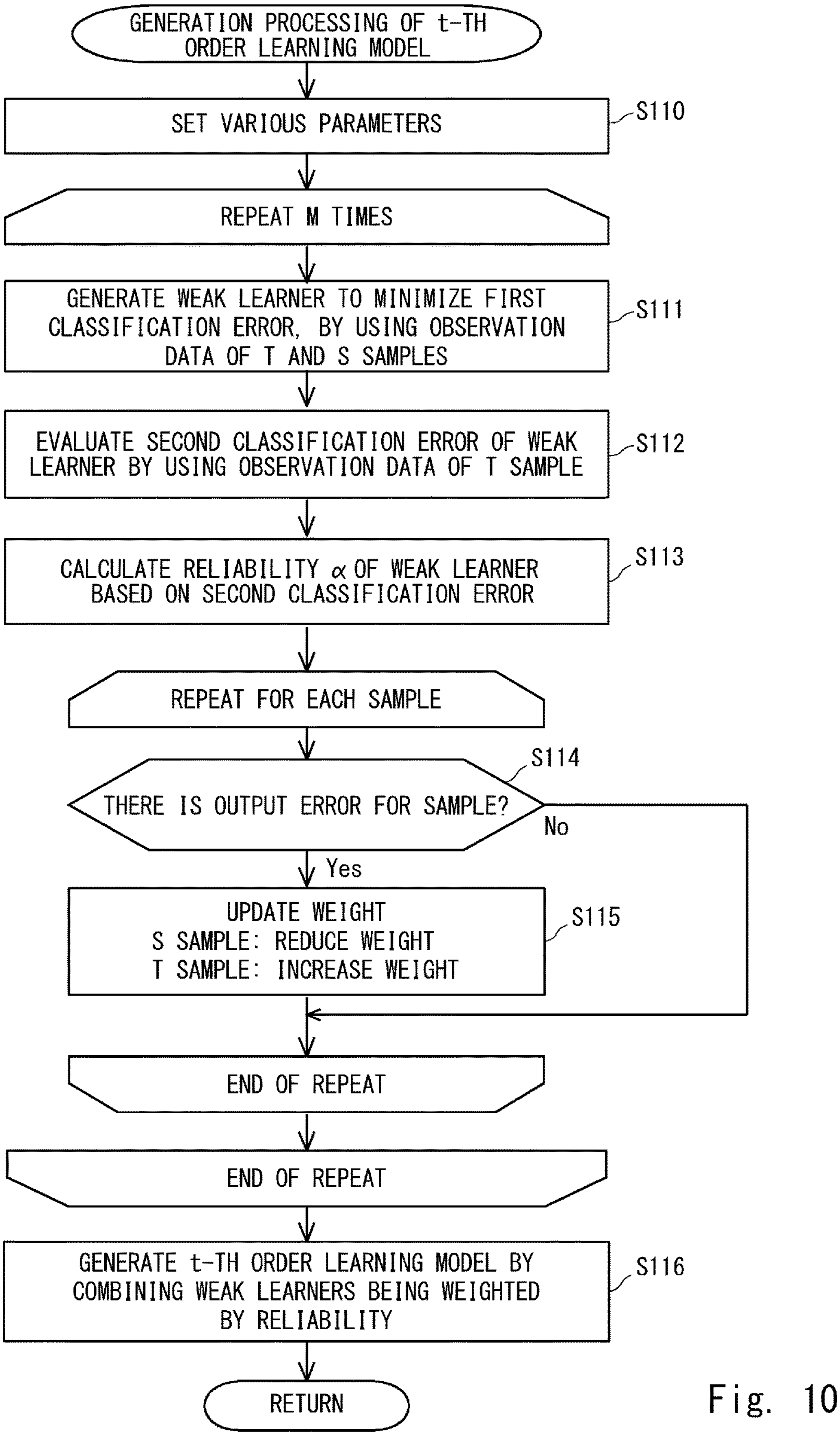
FIG. 10 is a flowchart illustrating a flow of a generation method of a t-th order learning model according to the second example embodiment.

FIG. 10 is a flowchart illustrating a flow of a generation method of a t-th order learning model according to the second example embodiment when j=t. FIG. 11 is a diagram illustrating one example of an algorithm for generating the t-th order learning model according to the second example embodiment;

First, in step S110 in FIG. 10, the weak learner generation unit 14 of the generation unit 13*a* sets various parameters. Specifically, as illustrated in a paragraph 1 in FIG. 11, the weak learner generation unit 14 sets a coefficient $\alpha_{S,i}$ used for updating a S sample weight $\omega_i^S$. In addition, as illustrated in a paragraph 2 in FIG. 11, a weight $\omega_i$ ($\omega_i^T$ or $\omega_i^S$) for each sample is initialized.

Next, following processing indicated in steps S111 to S115 are repeated M times. M is predetermined.

In step S111 of iteration m, the weak learner generation unit 14 generates the m-th weak learner $T^{(m)}$ among the M weak learners included in the t-th order learning model $D^*_t$. At this time, the weak learner generation unit 14 uses the observation data d_TG, at the time t to the time T, of the T sample and the observation data d_SG, at the time t to the time T, of the S sample, which are weighted by the weight $\omega_i$ being set for each sample. Then, the weak learner generation unit 14 finds a weak learner in which the first classification error $err_1$ evaluated by using the observation data of the T sample and the observation data of the S sample is minimized, and generates the found weak learner as the weak learner $T^{(m)}$. Specifically, the weak learner generation unit 14 generates the weak learner $T^{(m)}$ by using the expression (8) as illustrated in a paragraph 5 in FIG. 11.

In step S112, the reliability calculation unit 15 of the generation unit 13*a* evaluates the second classification error $err_2^{(m)}$ of the weak learner $T^{(m)}$ by using the observation data at the time t of the T sample. Specifically, as illustrated in paragraphs 6 to 7 in FIG. 11, the reliability calculation unit 15 calculates the second classification error by using the equation (4).

In S113, the reliability calculation unit 15 calculates the reliability $\alpha_j^{(m)}$ of the weak learner $T^{(m)}$, based on the second classification error $err_2^{(m)}$. Specifically, as illustrated in a paragraph 8 in FIG. 11, the reliability calculation unit 15 calculates the reliability by using the equation (3).

Next, the weight update unit 16 of the generation unit 13*a* repeats processing indicated in S114 to S115 for each sample. Note that, in the present processing, the weight update unit 16 executes different pieces of processing between the T sample and the S sample. Specifically, the weight update unit 16 increases the weight $\omega_i^T$ for a sample of the T sample having the output error of the weak learner $T^{(m)}$ with respect to the observation data d_TG at the time t (Yes in S114→S115). In addition to or instead of this, the weight update unit 16 reduces the weight $\omega_i^S$ for a sample of the S sample having the output error of the weak learner $T^{(m)}$ with respect to the observation data d_SG at the time t (Yes in S114→S115). On the other hand, regardless of the T sample and the S sample, the weight update unit 16 does not update the weight for a sample having the output error equal to or less than a predetermined amount or having no output error (No in S114). As a result, the observation data of the sample being optimal at the time t have a relatively larger degree of influence than the observation data of the sample that are not optimal at the time t, as repetition proceeds. In other words, the t-th order learning model can be generated with emphasis on the sample being optimal at the time t rather than the sample that is not optimal. Therefore, estimation accuracy of the t-th order learning-model $D^*_t$ is improved.

More specifically, the weight update unit 16 may update the weights $\omega_i^T$ and $\omega_i^S$ in the manner illustrated in paragraphs 9 to 11 in FIG. 11. In other words, the weight update unit 16 may increase the weight $\omega_i^T$ according to the reliability $\alpha_t^{(m)}$ of the weak learner $T^{(m)}$ for the sample of the T sample having the output error of the weak learner $T^{(m)}$ with respect to the observation data d_TG at the time t. Since the reliability $\alpha_t^{(m)}$ is calculated based on the second classification error $err_2^{(m)}$ as indicated in the equation (3), the weight $\omega_i^T$ is increased according to the second classification error $err_2^{(m)}$. Therefore, for a sample being optimal at the time t, the larger the second classification error, the larger the degree of influence as the repetition proceeds. As a result, it is possible to place more emphasis on a sample being optimal at the time t in generation of the t-th order learning model than a sample that is not optimal. Consequently, the estimation accuracy of the t-th order learning model $D^*_t$ is further improved. Note that, the weight update unit 16 may reduce the weight $\omega_i^S$ according to the coefficient $\alpha_{S,i}$ being set in S110, that is, the predetermined coefficient $\alpha_{S,i}$, for the sample of the S sample having the output error of the weak learner $T^{(m)}$ with respect to the observation data d_SG at the time t.

After executing the processing indicated in S114 to S115 for all the samples, the weight update unit 16 proceeds processing to the next iteration m+1.

By repeating this M times, the generation unit 13*a* generates M weak learners $T^{(m)}$ (a first weak learner $T^{(1)}$, a second weak learner $T^{(2)}$, . . . , a M-th weak learner $T^{(M)}$) and reliability $\alpha_t^{(m)}$ (first reliability $\alpha_t^{(1)}$, second reliability $\alpha_t^{(2)}$, . . . , M-th reliability $\alpha_t^{(M)}$) associated to each weak learner.

Then, in S116, the learning model generation unit 17 of the generation unit 13*a* generates the t-th order learning model $D^*_t$ by combining each of the generated M pieces of weak learners $T^{(m)}$ weighted by the associated reliability $\alpha_t^{(m)}$. Specifically, as illustrated in a paragraph 13 in FIG. 11, the learning model generation unit 17 adds up each weak learner $T^{(m)}$ weighted by the associated reliability $\alpha_t^{(m)}$ to each other by using the equation (2), and thereby generates the t-th order learning model $D^*_t$.

As described above, according to the second example embodiment, similarly to the first example embodiment, it is possible to increase training data used for generating a learning model, particularly for generating a weak learner. As a result, it is possible to generate a learning model that estimates in highly accuracy an action at each time according to each individual subject.

In addition, in a process of generating a plurality of weak learners included in the learning model, the weight $\omega_i$ indicating a degree of influence is updated in such a way that the T sample has a larger degree of influence on learning than the S sample. Therefore, the estimation accuracy of the learning model is improved.

Third Example Embodiment

Next, a third example embodiment of the present disclosure will be described. In the third example embodiment, when generating a plurality of weak learners included in a t-th order learning model $D^*_t$, a result of generation of a (t+1)-th order learning model $D^*_{t+1}$ is considered. Specifically, a generation unit 13*a* determines a weight $\omega_i^S$ indicating a degree of influence of a S sample in learning of a weak learner included in the t-th order learning model $D^*_t$, according to an amount that the S sample is determined to be not optimal by using the (t+1)-th order learning model $D^*_{t+1}$.

Since a flow of a generation method of the t-th order learning model according to the third example embodiment is basically similar to steps illustrated in FIG. 10, only a different part will be described below with reference to FIG. 12. FIG. 12 is a diagram illustrating one example of an algorithm for generating the t-th order learning model $D^*_t$ according to the third example embodiment.

First, in step S110, a weak learner generation unit 14 determines an initial value of the weight $\omega_i^S$, based on an output error $\tau_i$ of the (t+1)-th order learning model $D^*_{t+1}$ with respect to observation data d_SG at time t of the S sample. The above-described output error $\tau_i$ corresponds to the above-described "amount determined to be not optimal". Specifically, as illustrated in a paragraph 1 in FIG. 12, the weak learner generation unit 14 determines an initial value of a coefficient $\alpha_{S,i}$ for determining an initial value of the weight $\omega_i^S$, based on the output error $\tau_i$. As a result, a degree of influence of the S sample can be made different depending on the output error $\tau_i$ even among the S samples. For example, the weak learner generation unit 14 can be designed in such a way that the S sample having a larger output error $\tau_i$ has a smaller degree of influence by reducing the initial value of the weight $\omega_i^S$, and the S sample having a smaller output error $\tau_i$ has an influence on the learning of the weak learner.

In addition, a weight update unit 16 also determines a weight reduction amount when the weight $\omega_i^S$ of the S sample is updated in S115, based on the output error $\tau_i$. Specifically, as illustrated in a paragraph 10 in FIG. 12, the weight update unit 16 updates the weight $\omega_i^S$ used in subsequent iteration m+1 in such a way as to be a negative correlation with the coefficient $\alpha_{S,i}$ including the output error $\tau_i$. As a result, the S sample having the larger output error $\tau_i$ can have the larger weight reduction amount, and thereby the degree of influence can be reduced each time the number of pieces of iteration increases. Therefore, even between the S samples, the degree of influence of the S sample can be significantly made different depending on the output error $\tau_i$.

In FIG. 12, the generation unit 13*a* executes both the determination of the initial value of the weight $\omega_i^S$, based on the output error $\tau_i$ and the determination of the reduction amount when the weight $\omega_i^S$ is updated, based on the output error $\tau_i$, but either one of them may be omitted.

Fourth Example Embodiment

Next, a fourth example embodiment of the present disclosure will be described. In the fourth example embodiment, when a generation unit 13*a* generates a t-th order learning model $D^*_t$, information acquired by subtracting a predetermined amount from an amount of an effect Y included in observation data at time t+1 is used as an effect at the time t+1 for a S sample. Thus, it is possible to explicitly teach in generation of the t-th order learning model $D^*_t$ that the S sample is a sample being determined not to be optimal in a (t+1)-th order learning model $D^*_{t+1}$.

FIG. 13 is a diagram for describing a deriving method of a weak learner $T^{(m)}$ included in the t-th order learning model $D^*_t$ according to the fourth example embodiment. In the fourth example embodiment, the weak learner $T^{(M)}$ can be derived from the following expression (12) instead of the expression (8).

[Mathematical 12]

$$\arg\min \frac{1}{n}\sum_{i=1}^{n} \frac{S_{t+1,i} + \left(\sum_{j=t+1}^{T} Y_{ji}\right)\prod_{j=t+1}^{T} \mathbb{I}(A_{ji} = D_I^*(X_{ji}))}{\prod_{j=t+1}^{T} \pi_{A_{ji}}(X_{ji})} \frac{Y_i}{\pi_{A_i}(X_i)} \exp\left(-\frac{1}{K} Z_i^T g(X_i)\right) \tag{12}$$

As illustrated in FIG. 13, the expression (12) is different from the expression (8) in that it has a block 900" instead of the block 900'. In the block 900", $S_{t+1,i}$ associated to an effect at time t+1 is given as the following equation (13) (block 120) by using $Y_{t+1,i}$ included in observation data.

[Mathematical 13]

$$S_{t+1,i} = \begin{cases} Y_{(t+1),i} & \text{if } \mathbb{I}(A_{(t+1),i} = D^*_{t+1}(X_{t+1,i}))\ i \in \text{Target}, \\ \lambda Y_{(t+1),i} & \text{if } \mathbb{I}(A_{(t+1),i} = D^*_{t+1}(X_{t+1,i}))\ i \in \text{Source}, \\ 0 & \text{otherwise} \end{cases} \tag{13}$$

$\lambda$ is an adjustment parameter less than 1. By multiplying $\lambda$ by the effect Y at the time t+1 of the S sample, an amount of the effect Y at the time t+1 can be reduced for the S sample. Meanwhile, for a T sample, the amount of the observed effect Y is used as an amount of an effect at time t+1. As a result, a learning model can be generated in consideration of the S sample.

Note that, the $\lambda$ applied to the effect at time t+1 of the S sample may be determined for each sample, based on an output error $\tau_i$ of the (t+1)-th order learning model $D^*_{t+1}$ with respect to observation data at time t+1 of the sample. As one example, a weak learner generation unit 14 may assign $\lambda$=0.9 to the S sample having the small output error $\tau_i$, and assign $\lambda$=0.5 to the S sample having the large output error $\tau_i$. By doing so, the weak learner generation unit 14 can increase an amount to be subtracted from the effect Y at the time t+1 as the S sample having the larger output error $\tau_i$, that is, as the S sample being farther from an optimum.

Fifth Example Embodiment

Next, a fifth example embodiment of the present disclosure will be described. In the fifth example embodiment, a generation unit 13*a* uses cost-sensitive learning when generating a weak learner included in a learning model.

FIG. 14 is a diagram for describing a deriving method of a weak learner $T^{(m)}$ included in a t-th order learning model $D^*_t$ according to the fifth example embodiment.

In the fifth example embodiment, the weak learner $T^{(m)}$ can be derived from the following expression (14) instead of the expression (8).

[Mathematical 14]

$$\arg\min\frac{1}{n}\sum_{i=1}^{n}\left(\frac{Y_{t+1i}+\left(\sum_{j=t+2}^{T}Y_{ji}\right)\prod_{j=t+2}^{T}\mathbb{I}(A_{ji}=D_I^*(X_{ji}))}{\prod_{j=t+1}^{T}\pi_{A_{ji}}(X_{ji})}\frac{Y_i}{\pi_{A_i}(X_i)}C^*(A_i,D^*(X_i))\right)\exp\left(-\frac{1}{K}z_i^T f(X_i)\right)\tag{14}$$

Herein. $D^*(X_i)$ represents an index of a largest element of a vector $f(X_i)=\beta^1 g^1(X_i)+\beta^2 g^2(X_i)+\ldots+\beta^M g^M(X_i)$. In other words, $D^*(X_i)=\text{argmax } f^{(M)}(X_i)$.

The expression (14) is different from the expression (8) in that a cost function C* (block 130 in FIG. 14) is introduced into $\Sigma$. The cost function C* provides a penalty when there is an output error of the weak learner $T^{(m)}$, that is, when the weak learner $T^{(m)}$ makes erroneous decision. For example, the cost function C* is designed in such a way as to provide a large penalty when the output error of the weak learner $T^{(m)}$ is large, and provide a small penalty when the output error of the weak learner $T^{(m)}$ is small.

For example, the cost function C* when K=5 is given by the following equation (15). Note that, C*(p, q) represents an element of a p-th column and a q-th row of a matrix (cost matrix) indicating the cost function.

[Mathematical 15]

$$\begin{pmatrix}1.0 & 0.1 & 0.2 & 0.3 & 0.4\\ 0.1 & 1.0 & 0.1 & 0.2 & 0.3\\ 0.2 & 0.1 & 1.0 & 0.1 & 0.2\\ 0.3 & 0.2 & 0.1 & 1.0 & 0.1\\ 0.4 & 0.3 & 0.2 & 0.1 & 1.0\end{pmatrix}\tag{15}$$

A non-diagonal component of the C* functions when there is the output error of the weak learner $T^{(m)}$, that is, when the weak learner $T^{(m)}$ makes erroneous decision. Specifically, the non-diagonal component of the C* is set in such a way that the penalty becomes large when the output error is large.

Since a flow of a generation method of the t-th order learning model $D^*_t$ according to the fifth example embodiment is basically similar to steps illustrated in FIG. 10, only a different part will be described below with reference to FIG. 15. FIG. 15 is a diagram illustrating one example of an algorithm for generating the t-th order learning model $D^*_t$ according to the fifth example embodiment.

In S111, a weak learner generation unit 14 generates the weak learner $T^{(m)}$ by using the expression (14) instead of the expression (8), as illustrated in a paragraph 5 in FIG. 15. Therefore, the weak learner $T^{(m)}$ is learned in such a way that an action estimated by the weak learner $T^{(m)}$ and an action A observed in a sample are not separated from each other as much as possible. As a result, the weak learner $T^{(m)}$ can more clearly classified a S sample being closer to an optimum and a S sample being farther from the optimum. In other words, the weak learner $T^{(m)}$ can more accurately find the S sample being closer to the optimum.

Figure 16:
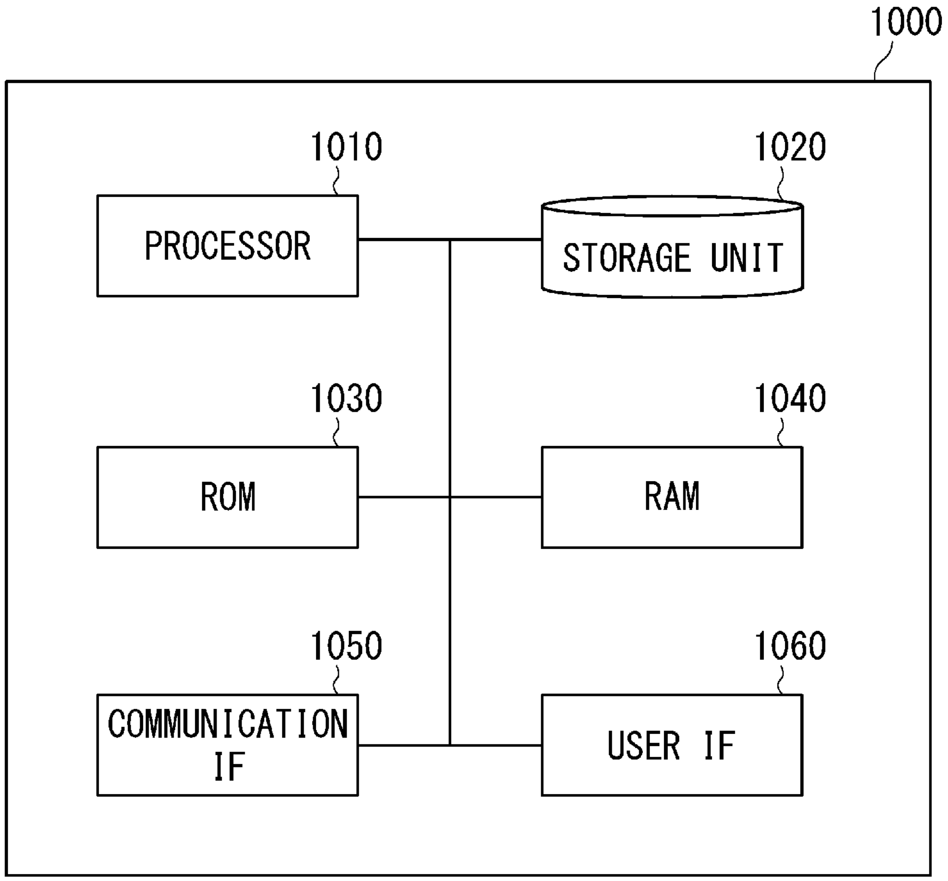
FIG. 16 is a diagram illustrating a configuration example of a computer.

Next, physical configurations of learning model generation apparatuses 10 and 10*a* and an estimation apparatus 30 included in a system 1 will be described. FIG. 16 is a diagram illustrating a configuration example of a computer that can be used as the learning model generation apparatuses 10 and 10*a* or the estimation apparatus 30. A computer 1000 includes a processor 1010, a storage unit 1020, a read only memory (ROM) 1030, a random access memory (RAM) 1040, a communication interface (IF) 1050, and a user interface 1060.

The communication interface 1050 is an interface for connecting the computer 1000 and a communication network via a wired communication means, a wireless communication means, or the like. The user interface 1060 includes a display unit, for example, such as a display. In addition, the user interface 1060 includes an input unit such as a keyboard, a mouse, and a touch panel. Note that, the user interface 1060 is not essential.

The storage unit 1020 is an auxiliary storage apparatus capable of holding various types of data. The storage unit 1020 is not necessarily a part of the computer 1000, and may be an external storage apparatus, or may be a cloud storage connected to the computer 1000 via a network.

The ROM 1030 is a non-volatile storage apparatus. For example, a semiconductor memory apparatus such as a flash memory having a relatively small capacity is used for the ROM 1030. A program executed by the processor 1010 may be stored in the storage unit 1020 or the ROM 1030. The storage unit 1020 or the ROM 1030 stores various programs for achieving a function of each unit in the learning model generation apparatuses 10 and 10*a* or the estimation apparatus 30, for example.

The program can be stored and provided to the computer 1000 using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM, etc.). The program may be provided to a computer using any type of transitory computer readable media. Examples of transitory computer readable media include electric signals, optical signals, and electromagnetic waves. Transitory computer readable medium can provide the program to a computer via a wired communication line (e.g., electric wires, and optical fibers) or a wireless communication line.

The RAM 1040 is a volatile storage apparatus. Various types of semiconductor memory apparatuses such as a dynamic random access memory (DRAM) and a static random access memory (SRAM) are used for the RAM 1040. The RAM 1040 may be used as an internal buffer for temporarily storing data and the like. The processor 1010 develops a program stored in the storage unit 1020 or the ROM 1030 to the RAM 1040, and executes the program. The processor 1010 may be a central processing unit (CPU) or a graphics processing unit (GPU). When the processor 1010 executes the program, the function of each unit in the learning model generation apparatuses 10 and 10*a* or the estimation apparatus 30 can be achieved. The processor 1010 may include an internal buffer capable of temporarily storing data and the like.

Note that, the present disclosure is not limited to the above-described example embodiments, and can be appropriately modified without departing from the spirit.

It will be understood by those of ordinary skill in the art that various changes in form and details may be made therein without departing from the spirit and scope of the present disclosure as defined by the claims.

The first to fifth example embodiments can be combined as desirable by one of ordinary skill in the art.

An example advantage according to the present disclosure is to provide a learning model generation apparatus, a learning model generation method, and a program that suitably generate a learning model for estimating an action plan tailored to a subject.

Some or all of the above-described example embodiments may be described as the following supplementary notes, but are not limited thereto.

(Supplementary Note 1)

A machine learning model generation apparatus including:

a movement unit that executes movement processing of moving a sample, among a plurality of samples included in a target sample group, having an output error of a (t+1)-th order machine learning model with respect to observation data at time t+1 (t is a natural number) being larger than a predetermined amount, from the target sample group to a source sample group; and a generation unit that generates a plurality of weak learners by using at least observation data from time t to time T of at least one sample included in the target sample group after the movement processing and at least one sample included in the source sample group after the movement processing, and generates a t-th order machine learning model, based on at least each of the plurality of generated weak learners, and a classification error being evaluated, for each of the plurality of generated weak learners, by using observation data at time t of the at least one sample included in the target sample group after the movement processing, wherein the observation data include at least a state and an action of a sample at a specific time until time T, and the t-th order machine learning model outputs an action at time t by using at least a state at time t as an input.

(Supplementary Note 2)

The machine learning model generation apparatus according to supplementary note 1, wherein the movement unit moves, after discarding a sample included in the source sample group, a sample having an output error of a (t+1)-th order machine learning model with respect to observation data at time t+1 being larger than a predetermined amount, to a source sample group.

(Supplementary Note 3)

The machine learning model generation apparatus according to supplementary note 1 or 2, wherein the plurality of weak learners includes at least a first weak learner and a second weak learner, and the generation unit generates the first weak learner by using observation data being weighted by a weight being set for each sample, increases a weight for a sample, among samples included in the target sample group after the movement processing, having an output error of the first weak learner with respect to observation data at time t being larger than a predetermined amount, reduces a weight for a sample, among samples included in the source sample group after the movement processing, having an output error of the first weak learner with respect to observation data at time t being larger than a predetermined amount, and generates the second weak learner by using observation data being weighted by a weight being updated for each sample.

(Supplementary Note 4)

The machine learning model generation apparatus according to supplementary note 3, wherein the generation unit increases a weight according to the classification error being evaluated for the first weak learner, for a sample, among samples included in the target sample group after the movement processing, having an output error of the first weak learner with respect to observation data at time t being larger than a predetermined amount, and reduces a weight according to a predetermined coefficient, for a sample, among samples included in the source sample group after the movement processing, having an output error of the first weak learner with respect to observation data at time t being larger than a predetermined amount.

(Supplementary Note 5)

The machine learning model generation apparatus according to supplementary note 3 or 4, wherein the generation unit determines, for each sample included in the source sample group after the movement processing, at least one of an initial value of a weight of observation data of the sample, and a reduction amount of a weight when the weight of the sample is updated, based on an output error of a (t+1)-th order machine learning model with respect to observation data at time t+1 of the sample.

(Supplementary Note 6)

The machine learning model generation apparatus according to supplementary note 5, wherein the generation unit reduces, for each sample included in the source sample group after the movement processing, an initial value of a weight of observation data of the sample, as an output error of a (t+1)-th order machine learning model with respect to observation data at time t+1 of the sample is larger, or increases, for each sample included in the source sample group after the movement processing, a reduction amount of a weight when the weight of the sample is updated, as an output error of a (t+1)-th order machine learning model with respect to observation data at time t+1 of the sample is larger.

(Supplementary Note 7)

The machine learning model generation apparatus according to any one of supplementary notes 1 to 6, wherein the observation data include an amount of an effect acquired by an action at a specific time in a sample having a state at the specific time until time T.

(Supplementary Note 8)

The machine learning model generation apparatus according to supplementary note 7, wherein the generation unit uses, when the plurality of weak learners is generated, information acquired by subtracting an amount according to an output error of a (t+1)-th order machine learning model from an amount of an effect included in observation data at time t+1, for each sample included in the source sample group after the movement processing, as an effect at time t+1 of the sample.

(Supplementary Note 9)

The machine learning model generation apparatus according to supplementary note 8, wherein the generation unit increases an amount of reduction as a sample has a larger output error of a (t+1)-th order machine learning model at time t+1 when the amount of the effect is reduced.

(Supplementary Note 10)

The machine learning model generation apparatus according to any one of supplementary notes 1 to 9, wherein the generation unit uses cost-sensitive learning when each of the plurality of weak learners is generated.

(Supplementary Note 11)

The machine learning model generation apparatus according to any one of supplementary notes 1 to 10, wherein the generation unit calculates, for each of the plurality of generated weak learners, reliability of the weak learner, based on at least the classification error being evaluated, for the weak learner, by using observation data at time t of at least one sample included in the target sample group after the movement processing, and generates the t-th order machine learning model by combining each of the plurality of generated weak learners being weighted by associated reliability.

(Supplementary Note 12)

A machine learning model generation method including:

executing movement processing of moving a sample, among a plurality of samples included in a target sample group, having an output error of a (t+1)-th order machine learning model with respect to observation data at time t+1 (t is a natural number) being larger than a predetermined amount, from the target sample group to a source sample group;

generating a plurality of weak learners by using at least observation data from time t to time T of at least one sample included in the target sample group after the movement processing and at least one sample included in the source sample group after the movement processing; and generating a t-th order machine learning model, based on at least each of the plurality of generated weak learners, and a classification error being evaluated, for each of the plurality of generated weak learners, by using observation data at time t of the at least one sample included in the target sample group after the movement processing, wherein the observation data include at least a state and an action of a sample at a specific time until time T, and the t-th order machine learning model outputs an action at time t by using at least a state at time t as an input.

(Supplementary Note 13)

A program for causing a computer to execute:

movement processing of moving a sample, among a plurality of samples included in a target sample group, having an output error of a (t+1)-th order machine learning model with respect to observation data at time t+1 (t is a natural number) being larger than a predetermined amount, from the target sample group to a source sample group;

processing of generating a plurality of weak learners by using at least observation data from time t to time T of at least one sample included in the target sample group after the movement processing and at least one sample included in the source sample group after the movement processing; and processing of generating a t-th order machine learning model, based on at least each of the plurality of generated weak learners, and a classification error being evaluated, for each of the plurality of generated weak learners, by using observation data at time t of the at least one sample included in the target sample group after the movement processing, wherein the observation data include at least a state and an action of a sample at a specific time until time T, and the t-th order machine learning model outputs an action at time t by using at least a state at time t as an input.

(Supplementary Note 14)

The machine learning model generation apparatus according to supplementary note 1, wherein the t-th order learning model outputs an action of a healthcare worker at the time t, the action having been optimized in order to maximize a treatment effect of a patient.

What is claimed is:

1. A system for dynamically generating an optimized treatment plan for a patient, the system comprising:

at least one memory configured to store instructions and observation data for a plurality of samples, wherein the observation data is classified into a target sample group, a source sample group, and a discarded sample group, the observation data including at least a state and an action of a sample;

a learning model storage apparatus configured to store, for each time t in a period from time t=1 to a final time T, a corresponding t-th order machine learning model; and at least one processor configured to execute the instructions to implement:

a learning model generation apparatus configured to sequentially generate a time-series of machine learning models for each time t from the final time T down to 1 by performing:

re-classifying a sample, among samples included in the target sample group, from the target sample group to the source sample group, when an output error of a previously generated (t+1)-th order machine learning model for the sample exceeds a predetermined amount;

generating a plurality of weak learners for a t-th order machine learning model by using observation data from both the samples classified into the target sample group and the samples classified into the source sample group;

generating a t-th order machine learning model, based on the plurality of generated weak learners, and a classification error evaluated, for each weak learner using only the observation data of the samples in the target sample group; and for a subsequent learning step at time t−1, re-classifying all samples currently in the source sample group into the discarded sample group, thereby initializing the source sample group so as to consider only a sample that is optimal until the latest but is not optimal only the latest in generation of the machine learning model;

wherein the learning model generation apparatus is configured to store the generated t-th order machine learning model in the learning model storage apparatus; and an estimation apparatus communicably coupled to the learning model storage apparatus, the estimation apparatus configured to:

receive, at a current time t, observation data including a current state of the patient;

read, from the learning model storage apparatus, the t-th order machine learning model corresponding to the current time t;

input the current state of the patient into the read t-th order machine learning model to determine an action that maximizes a sum of effects acquired by the patient from the time t to the final time T; and output the determined action via a user interface including a display unit as part of the dynamically generated optimized treatment plan for the patient.

2. The machine learning model generation apparatus according to claim 1, wherein the at least one processor is configured to execute the instructions to:

move, after discarding a sample included in the source sample group, a sample having an output error of a (t+1)-th order machine learning model with respect to observation data at time t+1 being larger than a predetermined amount, to a source sample group.

3. The machine learning model generation apparatus according to claim 1, wherein the plurality of weak learners comprises at least a first weak learner and a second weak learner, and the at least one processor is configured to execute the instructions to:

generate the first weak learner by using observation data being weighted by a weight being set for each sample, increase a weight for a sample, among samples included in the target sample group after the movement processing, having an output error of the first weak learner with respect to observation data at time t being larger than a predetermined amount, reduce a weight for a sample, among samples included in the source sample group after the movement processing, having an output error of the first weak learner with respect to observation data at time t being larger than a predetermined amount, and generate the second weak learner by using observation data being weighted by a weight being updated for each sample.

4. The machine learning model generation apparatus according to claim 3, wherein the at least one processor is configured to execute the instructions to:

increases a weight according to the classification error being evaluated for the first weak learner, for a sample, among samples included in the target sample group after the movement processing, having an output error of the first weak learner with respect to observation data at time t being larger than a predetermined amount, and reduces a weight according to a predetermined coefficient, for a sample, among samples included in the source sample group after the movement processing, having an output error of the first weak learner with respect to observation data at time t being larger than a predetermined amount.

5. The machine learning model generation apparatus according to claim 3, wherein the at least one processor is configured to execute the instructions to:

determine, for each sample included in the source sample group after the movement processing, at least one of an initial value of a weight of observation data of the sample, and a reduction amount of a weight when the weight of the sample is updated, based on an output error of a (t+1)-th order machine learning model with respect to observation data at time t+1 of the sample.

6. The machine learning model generation apparatus according to claim 5, wherein the at least one processor is configured to execute the instructions to:

reduces, for each sample included in the source sample group after the movement processing, an initial value of a weight of observation data of the sample, as an output error of a (t+1)-th order machine learning model with respect to observation data at time t+1 of the sample is larger, or increases, for each sample included in the source sample group after the movement processing, a reduction amount of a weight when the weight of the sample is updated, as an output error of a (t+1)-th order machine learning model with respect to observation data at time t+1 of the sample is larger.

7. The machine learning model generation apparatus according to claim 1, wherein the observation data include an amount of an effect acquired by an action at a specific time in a sample having a state at the specific time until time T.

8. The machine learning model generation apparatus according to claim 7, wherein the at least one processor is configured to execute the instructions to: use, when the plurality of weak learners is generated, information acquired by subtracting an amount according to an output error of a (t+1)-th order machine learning model from an amount of an effect included in observation data at time t+1, for each sample included in the source sample group after the movement processing, as an effect at time t+1 of the sample.

9. The machine learning model generation apparatus according to claim 8, wherein the at least one processor is configured to execute the instructions to: increase an amount of reduction as a sample has a larger output error of a (t+1)-th order machine learning model at time t+1 when the amount of the effect is reduced.

10. The machine learning model generation apparatus according to claim 1, wherein the at least one processor is configured to execute the instructions to: use cost-sensitive learning when each of the plurality of weak learners is generated.

11. The machine learning model generation apparatus according to claim 1, wherein the at least one processor is configured to execute the instructions to:

calculate, for each of the plurality of generated weak learners, reliability of the weak learner, based on at least the classification error being evaluated, for the weak learner, by using observation data at time t of at least one sample included in the target sample group after the movement processing, and generate the t-th order machine learning model by combining each of the plurality of generated weak learners being weighted by associated reliability.

12. A machine learning model generation method comprising:

obtaining observation data for a plurality of samples, wherein the observation data is classified into a target sample group, a source sample group, and a discarded sample group, the observation data including at least a state and an action of a sample;

sequentially generate a time-series of machine learning models for each time t from the final time T down to 1 by performing:

re-classifying a sample, among samples included in the target sample group, from the target sample group to the source sample group, when an output error of a previously generated (t+1)-th order machine learning model for the sample exceeds a predetermined amount;

generating a plurality of weak learners for a t-th order machine learning model by using observation data from both the samples classified into the target sample group and the samples classified into the source sample group;

generating a t-th order machine learning model, based on the plurality of generated weak learners, and a classification error evaluated, for each weak learner using only the observation data of the samples in the target sample group; and for a subsequent learning step at time t−1, re-classifying all samples currently in the source sample group into the discarded sample group, thereby initializing the source sample group so as to consider only a sample that is optimal until the latest but is not optimal only the latest in generation of the machine learning model;

storing the generated t-th order machine learning model;

receiving, at a current time t, observation data including a current state of the patient;

reading the t-th order machine learning model corresponding to the current time t;

inputting the current state of the patient into the read t-th order machine learning model to determine an action that maximizes a sum of effects acquired by the patient from the time t to the final time T; and outputting the determined action via a user interface including a display unit as part of the dynamically generated optimized treatment plan for the patient.

13. A non-transitory computer readable medium storing a program for causing a computer to execute:

obtaining observation data for a plurality of samples, wherein the observation data is classified into a target sample group, a source sample group, and a discarded sample group, the observation data including at least a state and an action of a sample;

sequentially generate a time-series of machine learning models for each time t from the final time T down to 1 by performing:

re-classifying a sample, among samples included in the target sample group, from the target sample group to the source sample group, when an output error of a previously generated (t+1)-th order machine learning model for the sample exceeds a predetermined amount;

generating a plurality of weak learners for a t-th order machine learning model by using observation data from both the samples classified into the target sample group and the samples classified into the source sample group;

generating a t-th order machine learning model, based on the plurality of generated weak learners, and a classification error evaluated, for each weak learner using only the observation data of the samples in the target sample group; and for a subsequent learning step at time t−1, re-classifying all samples currently in the source sample group into the discarded sample group, thereby initializing the source sample group so as to consider only a sample that is optimal until the latest but is not optimal only the latest in generation of the machine learning model;

storing the generated t-th order machine learning model;

receiving, at a current time t, observation data including a current state of the patient;

reading the t-th order machine learning model corresponding to the current time t;

inputting the current state of the patient into the read t-th order machine learning model to determine an action that maximizes a sum of effects acquired by the patient from the time t to the final time T; and outputting the determined action via a user interface including a display unit as part of the dynamically generated optimized treatment plan for the patient.

14. The machine learning model generation apparatus according to claim 1, wherein the t-th order learning model outputs an action of a healthcare worker at the time t, the action having been optimized in order to maximize a treatment effect of a patient.

* * * * *